US007298280B2

(12) United States Patent
Voege et al.

(10) Patent No.: US 7,298,280 B2
(45) Date of Patent: Nov. 20, 2007

(54) LIGHTED FLUID FLOW INDICATION APPARATUS

(75) Inventors: James A. Voege, Carmel, IN (US); David A. Ferrer, Westfield, IN (US); Matthew G. Thie, Indianapolis, IN (US)

(73) Assignee: Ameriflo Inc., Carmel, IN (US)

( * ) Notice: Subject to any disclaimer, the term of this patent is extended or adjusted under 35 U.S.C. 154(b) by 326 days.

(21) Appl. No.: 10/862,525

(22) Filed: Jun. 7, 2004

(65) Prior Publication Data

US 2005/0011282 A1  Jan. 20, 2005

Related U.S. Application Data

(60) Provisional application No. 60/476,316, filed on Jun. 6, 2003.

(51) Int. Cl.
*G08B 21/00* (2006.01)
*H01H 35/24* (2006.01)
*H01H 35/40* (2006.01)
*A61M 11/00* (2006.01)
*A61M 15/00* (2006.01)
*G01F 1/24* (2006.01)
*G01L 7/00* (2006.01)
*G01L 7/08* (2006.01)

(52) U.S. Cl. ............... 340/606; 340/603; 340/612; 340/618; 340/626; 200/81.9 R; 200/83 R; 128/200.11; 128/200.14; 128/200.24; 73/861.56; 73/700; 73/715; 73/723

(58) Field of Classification Search ............... 340/606, 340/612, 626; 200/81.9 R, 83 R; 128/200.14, 128/200.24, 200.11; 73/861.56, 700, 715, 73/723
See application file for complete search history.

(56) References Cited

U.S. PATENT DOCUMENTS

| | | | |
|---|---|---|---|
| 1,573,371 A | 2/1926 | Bloch | |
| 4,586,136 A | 4/1986 | Lewis | |
| 4,654,643 A * | 3/1987 | Meisenheimer, Jr. | 340/626 |
| 4,668,943 A * | 5/1987 | Bunker et al. | 340/606 |
| 4,745,877 A * | 5/1988 | Chang | 116/274 |
| 4,763,114 A * | 8/1988 | Eidsmore | 340/606 |
| 4,800,373 A * | 1/1989 | Mayz | 340/626 |
| 4,945,337 A | 7/1990 | Huang | |
| 5,383,338 A * | 1/1995 | Bowsky et al. | 62/125 |
| 5,461,913 A | 10/1995 | Hinkle et al. | |
| 5,537,871 A | 7/1996 | Itsuji et al. | |
| 5,696,321 A | 12/1997 | Igarashi et al. | |
| 5,721,383 A * | 2/1998 | Franklin et al. | 73/861.77 |
| 6,032,525 A | 3/2000 | Suetake | |
| 6,067,022 A * | 5/2000 | Laswick et al. | 340/626 |
| 6,205,854 B1 | 3/2001 | Tohyama et al. | |
| 6,229,447 B1 * | 5/2001 | Hand et al. | 340/614 |
| 6,322,519 B1 | 11/2001 | Moulin | |
| 6,326,896 B1 * | 12/2001 | McDermott et al. | 340/626 |
| 6,338,279 B1 * | 1/2002 | Tsataros | 73/861.56 |

(Continued)

OTHER PUBLICATIONS

"Promotional items with customized logo around one dollar" from Haimel Electronics website; http://www.haimei.com; 2 pages; date: at least as early as Sep. 29, 2003.

*Primary Examiner*—Benjamin C. Lee
*Assistant Examiner*—Lam Pham
(74) *Attorney, Agent, or Firm*—Baker & Daniels LLP

(57) ABSTRACT

A fluid flow indication apparatus is provided for monitoring and giving an indication of fluid flow.

24 Claims, 20 Drawing Sheets

U.S. PATENT DOCUMENTS

| | | |
|---|---|---|
| 6,449,574 B1 | 9/2002 | Eryurek et al. |
| 6,467,939 B2 | 10/2002 | Deutsch et al. |
| 6,497,252 B1 | 12/2002 | Köhler et al. |
| 6,507,791 B2 | 1/2003 | Henry et al. |
| 6,510,741 B2 * | 1/2003 | Condrea et al. ............. 73/747 |
| 6,635,836 B1 * | 10/2003 | Beauchamp ........... 200/81.9 R |
| 7,051,594 B1 * | 5/2006 | Aziz ........................... 73/700 |
| 7,096,865 B1 * | 8/2006 | Coury et al. ........... 128/203.17 |
| 2003/0189492 A1 * | 10/2003 | Harvie .................... 340/573.1 |

* cited by examiner

NOMINAL CURRENT DRAW 7.9Ma

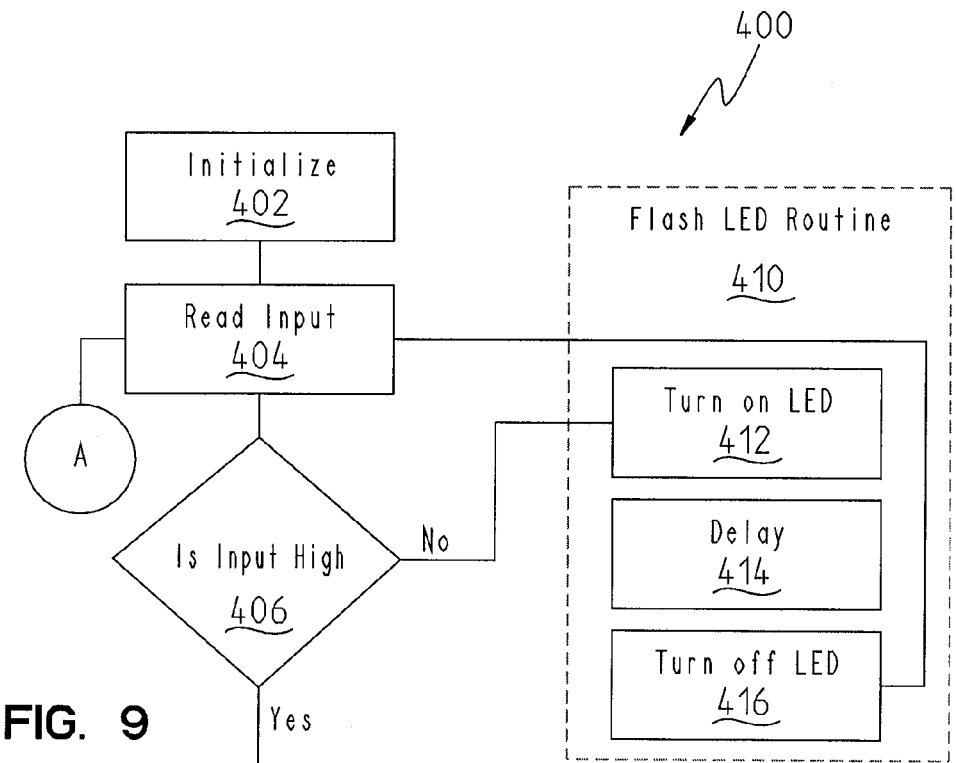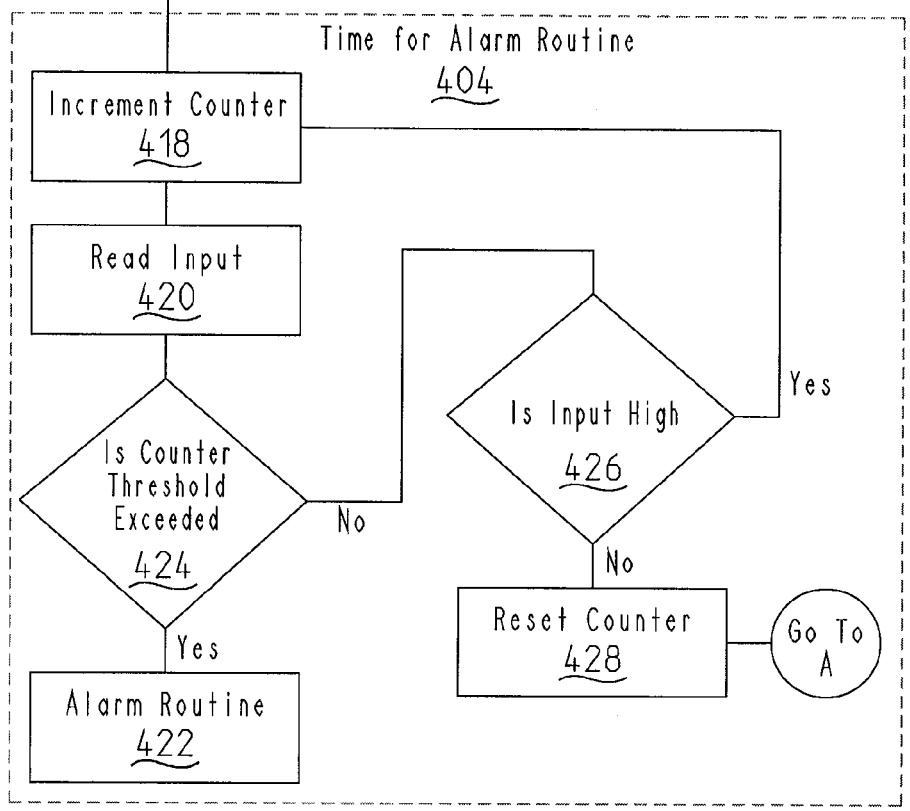
FIG. 9

LIGHTED FLUID FLOW INDICATION APPARATUS

BACKGROUND AND SUMMARY OF THE INVENTION

This application claims the benefit of U.S. Provisional Patent Application Ser. No. 60/476,316, filed Jun. 6, 2003, titled Lighted Fluid Flow Indication Apparatus, to Voege et al, the disclosure of which is expressly incorporated by reference herein.

The present invention relates generally to an indicator or monitor of fluid flow. More specifically, the present invention relates to a self-contained in-line fluid flow monitor including an indicator.

Industrial and medical gases are typically conducted through a conduit such as a tube or cannula from a storage tank to an implement that utilizes the gases or to a patient. Such gases are often clear and give no visual indication of their presence in the ambient air or their flow within the tubes. Therefore, it is desirable to have an indicator to provide an indication when gas is flowing through a tube. It is also desirable to provide an indication when the tube has been disconnected from a supply, a leak has occurred, or pressure in the tube has dropped below a predetermined level.

The present invention provides an indicator that is configured to be coupled directly to the gas supply tube or cannula. Therefore, the present invention provides an effective, inexpensive indicator to provide a visual, audible or other indication when gas is flowing through a tube, when the tube has been disconnected from a supply, or when pressure in the tube has dropped below a predetermined level due to a leak or pressure drop in the gas supply.

In one exemplary embodiment, a gas flow monitor is provided. The gas flow monitor comprising a housing having a fluid passage, an inlet and an outlet, the fluid passage configured to pass a gas introduced at the inlet to the outlet; a controller contained within the housing; a first indicator contained within the housing; a pressure sensitive switch in fluid communication with the fluid passage. The pressure sensitive switch having a first position indicating that the fluid passage contains at least a threshold pressure of a gas introduced through the inlet and a second position indicating the absence of a threshold pressure of a gas in the fluid passage, wherein the controller is configured to provide a first indication with the first indicator in response to the pressure sensitive switch being in the first position.

In another exemplary embodiment, a gas flow monitor is provided which is configured to be coupled in-line to a gas delivery system configured to convey a regulated amount of gas from a gas source to a patient. The gas delivery system including a first portion coupled to the gas source and a second portion coupled to a fluid dispensing device. The gas flow monitor comprising a housing having a fluid passage, an inlet and an outlet, the fluid passage configured to pass a gas introduced at the inlet to the outlet, the inlet configured to be coupled to the first portion of the gas delivery system and the outlet configured to be coupled to the second portion of the gas delivery system; and an indicator contained within the housing. The indicator configured to provide a first indication to indicate that the gas is being passed from the inlet to the outlet of the housing, the first indication being visible from an exterior of the housing.

An exemplary method is provided for monitoring of a gas delivery system configured to convey a regulated amount of gas from a gas source to a patient, the gas delivery system including a first portion coupled to the gas source and a second portion coupled to a fluid dispensing device. The method comprising the steps of: providing a portable gas flow monitor, the portable gas flow monitor comprising a housing, at least one indicator, and a sensor, the housing having an inlet configured to be coupled to the first portion of the gas delivery system, an outlet configured to be coupled to the second portion of the gas delivery system, and a fluid passage in fluid communication with the inlet and the outlet; sensing the amount of fluid in the fluid passage to determine if a threshold amount of gas is in the fluid passage; providing a first indication with the at least one indicator in response to a determination that a threshold amount of gas is in the fluid passage, the first indication including a visual cue; and providing a second indication with the at least one indicator in response to a determination less than a threshold amount of gas is in the fluid passage, the second indication including a audible cue.

An exemplary embodiment of a kit is provided for use with a source of regulated medical gas to deliver the gas to a patient. The kit comprising: a single lumen cannula having an inlet portion, a conduit, and a fluid dispensing member, the fluid dispensing member adapted to be received by the nostrils of the patient; and a portable gas flow monitor including a housing having an inlet, an outlet, and a fluid passage, a pressure sensitive switch in fluid communication with the fluid passage, a power supply, an indicator, and a circuit coupled to the indicator and the power supply, wherein the pressure sensitive switch completes the circuit thereby providing power to the indicator in response to the fluid passage containing at least a threshold amount of gas, the indicator providing a first indication when the circuit is complete.

Additional features of the disclosure will become apparent to those skilled in the art upon consideration of the following detailed description when taken in conjunction with the accompanying drawings.

BRIEF DESCRIPTION OF THE DRAWINGS

FIGS. 9 and 10 are flow diagrams of a first exemplary program executed by the microcontroller of the circuit schematic of FIG. 8;

DETAILED DESCRIPTION OF THE DRAWINGS

Figure 1:
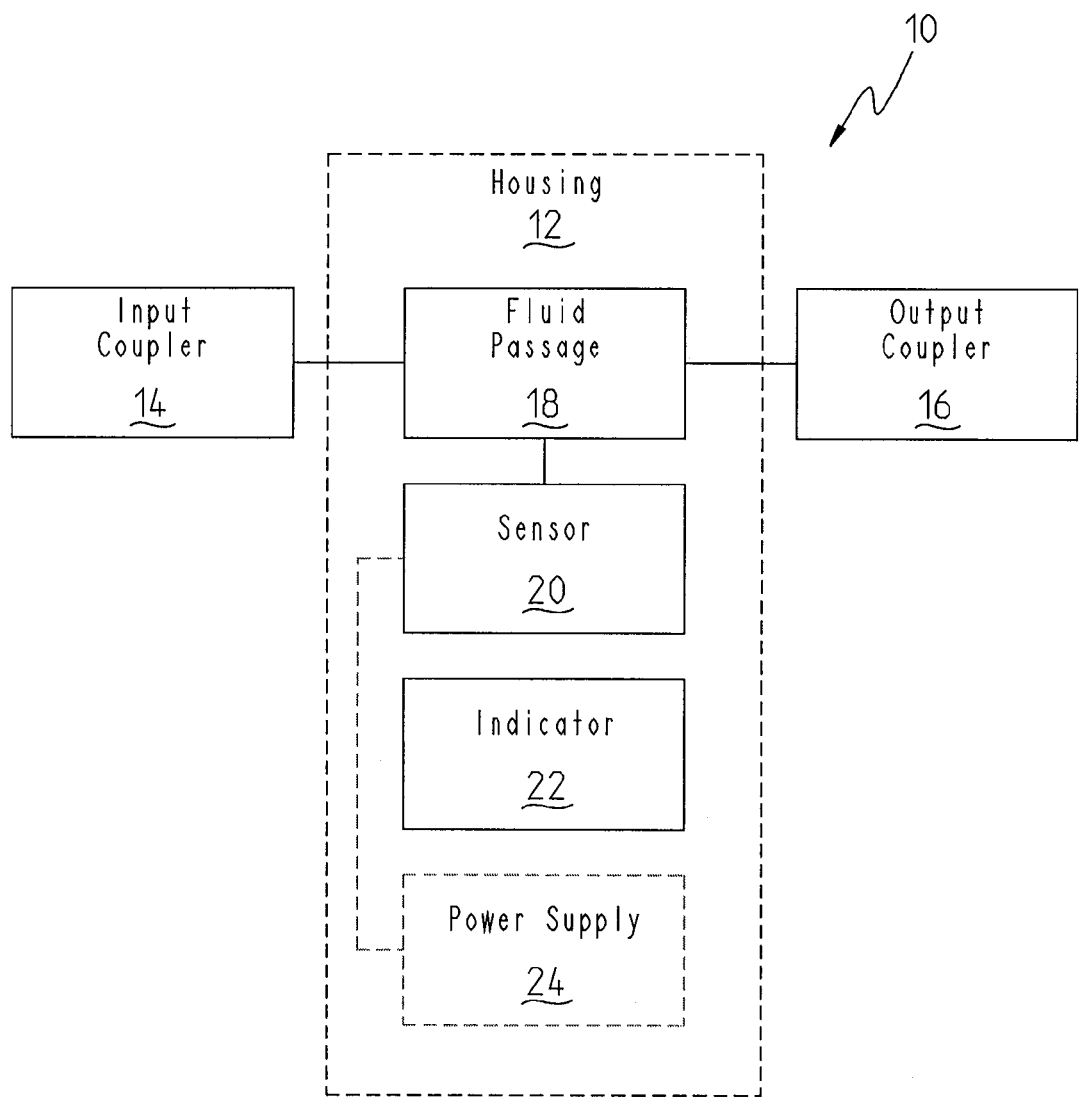
FIG. 1 is an illustration of an exemplary fluid flow monitor or indicator.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring to FIG. 1, a representation of a fluid flow monitor or fluid flow indicator 10 is shown. Fluid flow monitor 10 includes a housing 12 having an inlet coupler 14, an outlet coupler 16, and a fluid passage 18. Fluid passage 18 connects inlet coupler 14 and outlet coupler 16 in fluid communication such that fluid introduced at fluid inlet coupler 14 may be passed to fluid outlet coupler 16. Inlet coupler 14 and outlet coupler 16 are each configured to be coupled to an external device such as a conduit, a single lumen cannula, a fluid flow regulator, a source of regulated fluid, and other fluid transporting, utilizing, and/or delivery devices. In one example, inlet coupler 14 and/or outlet coupler 16 include a hose barb configured to receive a section of conduit or tubing. In another example, inlet coupler 14 and/or outlet coupler 16 include a threaded portion, such as an exterior threaded portion, the threaded portion sized to be received by a mating threaded portion on an external device. The above two examples are examples of removable couplers. In still a further example, input coupler and/or output coupler are permanently coupled to an external device by welding, with an adhesive, or other means.

Fluid flow monitor 10 further includes a sensor 20 and an indicator 22. As explained in more detail herein, sensor 20 is in fluid communication with fluid passage 18 and senses the pressure and/or flow of fluid in fluid passage 18. In one example, sensor 20 is a mechanical sensor, such as a diaphragm or a piston. In another example, sensor 20 is an electrical sensor, such as a temperature measuring resistor or electrical transducer.

Sensor 20 in one embodiment includes a flow sensor which provides a measurement of the flow rate of fluid in fluid passage 18. Sensor 20 in another embodiment includes a pressure sensor which provides a measurement of the fluid pressure in fluid passage 18.

In a preferred embodiment, input coupler is connected to a source of fluid, such as oxygen gas, outlet coupler 16 is coupled to a single lumen cannula which is positioned to provide fluid, such as oxygen gas, to the nostrils of a patient. Since the single lumen cannula is not capped, but is constantly permitting oxygen gas to escape to the nostrils of the patient a pressure sensor can be used to give an indication of fluid flow in the fluid passage 18 and to determine if the cannula has been disconnected from fluid monitor 10, if fluid monitor 10 has been disconnected from the fluid source, or if pressure in the fluid passage has dropped below a predetermined level due to a leak or pressure drop in the fluid supply. Assuming the gas delivery system, the single lumen cannula and fluid source, are operating correctly, the pressure sensor should expect to detect a pressure determined by calculating the back pressure expected due to the single lumen cannula and the expected flow rate from the fluid source. Fluid flow monitor 10 may be configured to operate with any length of tubing for the single lumen cannula, such as about 4 feet, about 8 feet, about 14 feet, or about 21 feet.

Further, fluid flow monitor or indicator 10 will detect a decrease in the pressure of fluid supplied by a flow regulator or other fluid source thereby indicating an empty fluid tank.

Indicator 22 provides at least one of a visual cue, an audible cue, a tactile cue, and a status signal to a remote device, each of which provides an indication to an observer or operator of the operation of the gas delivery system. Indicator 22 may be a light emitting element, such as an LED, a speaker, a vibrating member, and/or a rotating member. Wherein indicator 22 provides a visual cue, one of housing 12 and input coupler 14 or output coupler 16 is partially transparent or translucent such that the visual cue is visible from an exterior of housing 12. In an alternative embodiment, indicator 22 is mounted or coupled to an exterior of housing 12.

In one embodiment, an alarm is provided to indicate that the conduit has been removed from the output coupler 16 by including a fluid passage from fluid passage 18 to an exterior of the output coupler 16, the fluid passage configured to whistle when fluid exits the passage at the exterior of the output coupler. The whistle would serve as an alarm to indicate that the conduit has been removed from the output coupler 16. When the conduit is properly coupled to the output conduit, the opening of the fluid passage on the exterior of the output coupler 16 is covered by the conduit, hence the fluid passage cannot whistle.

As explained in more detail below sensor 20 may include an electrical circuit and/or controller which controls the operation of indicator 22. In such a case, a portable power supply, such as one or more button batteries, is included within housing 12 to provide power to sensor 20 and/or indicator 22.

In one embodiment, indicator 22 provides a first cue in response to the detection that the gas delivery system is operating properly. In another embodiment, indicator 22 provides a second cue in response to the detection that the gas delivery system is operating improperly. In a further embodiment, indicator 22 provides a third cue in response to the detection that the gas delivery system is operating properly and a fourth cue in response to the detection that the gas delivery system is operating improperly. Further, indicator 22 may provide a plurality of cues to indicate that the gas delivery system is operating properly and/or that the gas delivery system is operating improperly. For example, indicator may provide an audible cue if the gas delivery system is operating improperly and provide a signal to a remote device including status information that the gas delivery system is operating improperly.

Figure 2:
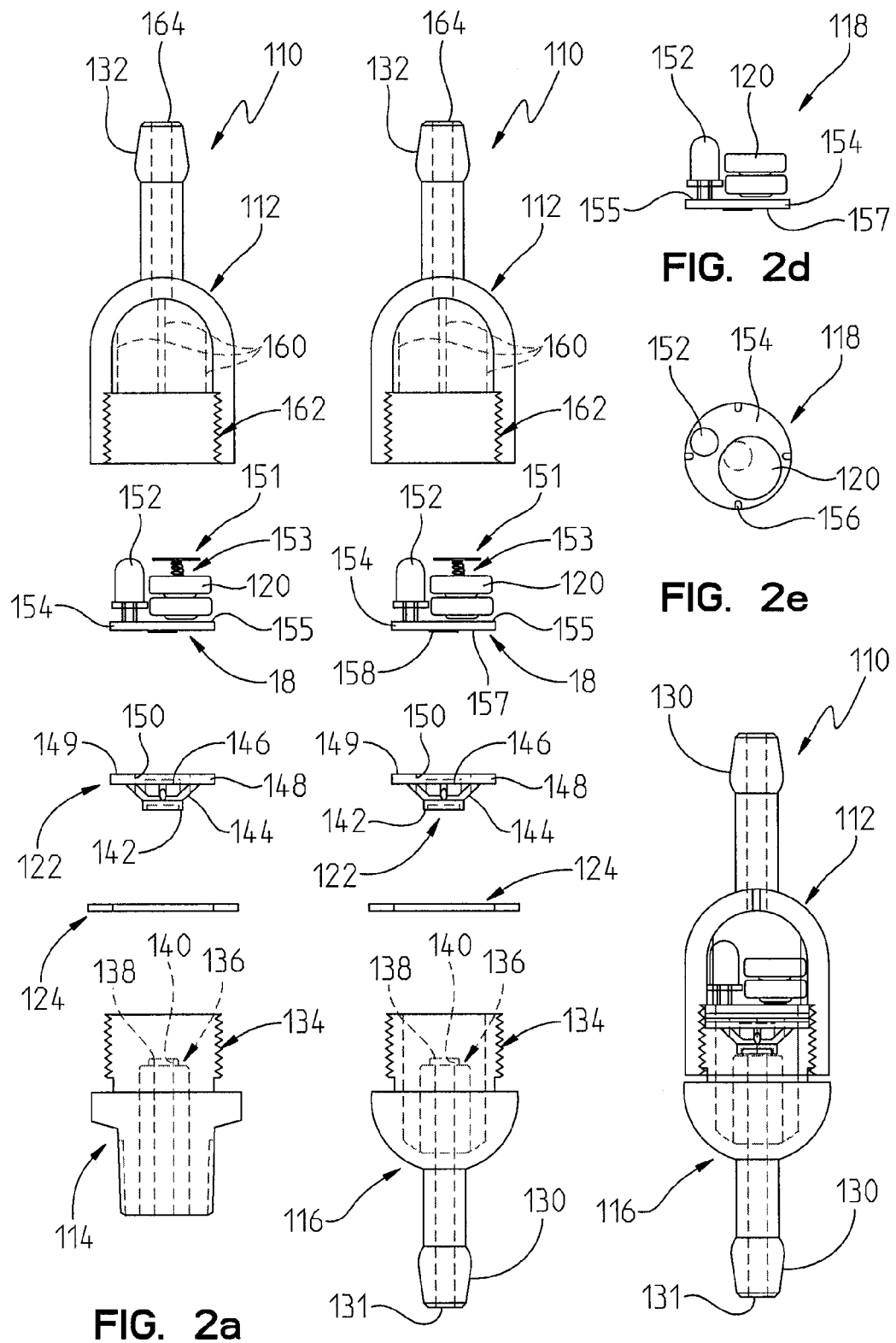
FIG. 2a is an exploded view of an exemplary fluid flow monitor or indicator having an input coupler configured to be coupled to a fluid regulator.
FIG. 2b is an exploded view of an exemplary fluid flow monitor having an input coupler configured to be coupled to a cannula.
FIG. 2c is a sectional view of the assembled fluid flow monitor of FIG. 2b.
FIG. 2d is a side elevation view of a circuit board, LED, and batteries of the fluid flow monitor of FIG. 2b.
FIG. 2e is a top view of the circuit board of 2d.

Referring to FIG. 2a a first exemplary fluid flow indicator or monitor is shown. Fluid flow indicator or monitor 110 is an in-line monitor for use with a conduit for fluids such as a cannula 128 as shown, for example, in FIGS. 3 and 4. Flow indicator 110 includes a housing 111, an electrical circuit 118, a plurality of batteries 120, a flexible diaphragm, such as rubber diaphragm 122, and a housing seal 124. Housing 111 includes an outlet housing 112 coupled to an inlet housing 114 or 116.

Figure 4:
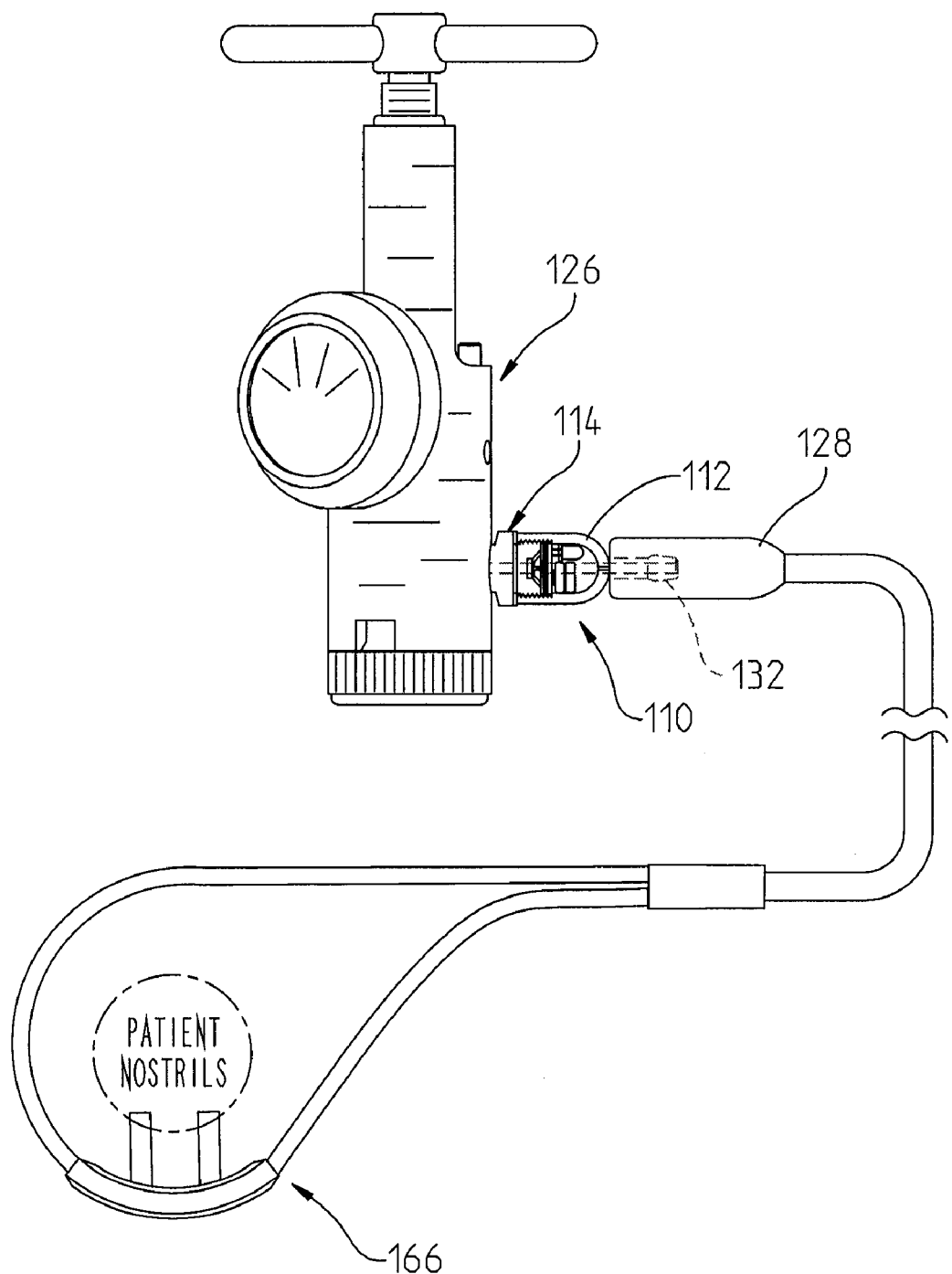
FIG. 4 is a sectional view of the fluid flow monitor with the regulator mount of FIG. 1 installed into a cannula and coupled to a regulator.

Inlet housing 114 connects flow indicator 110 directly to a regulator 126 as shown in FIG. 4. Inlet housing 116 includes an end barb 130 with input opening 131 configured to connect flow indicator 110 to cannula 128. Outlet housing 112 also includes a barbed end 132 configured to connect flow indicator 110 to cannula 128. Inlet housings 114,116 each include a threaded portion 134 and a diaphragm seat 136. Diaphragm seat 136 is illustratively a shoulder portion surrounding a rim 138 of an air inlet passage 140. When assembled, an inlet lip 142 of diaphragm 122 rests upon the diaphragm seat 136.

Diaphragm 122 includes the inlet lip 142, a flexible portion 144, a conductive pad 146, and a circuit support section 148. Inlet lip 142 may be integral with and extending from one side of flexible portion 144 or may be coupled to one side of flexible portion 144. Conductive pad 146 is located on the opposing side of flexible portion 144 from inlet lip 142. Circuit support section 148 is illustratively an annular section that includes an upper edge 149 and an aperture 150 therein sized to allow conductive pad 146 to extend therethrough. Circuit support 148 section is sized to fit within outlet housing 112 and to support electrical circuit 118 thereon. Flexible portion 144 is sized and shaped such that when in a normal, unbiased first position, conductive pad 146 is located below upper edge 149 of circuit support section 148. Flexible portion 144, when moved to a second, biased position as fluid such as gas flows through the housing 112, is deflected to move conductive pad 146 to a location above or even with upper edge 149 of circuit support section 148 to complete a conducting path as discussed below. As such, diaphragm 122 and conductive pad 146 act as a pressure sensitive switch.

Figure 7:
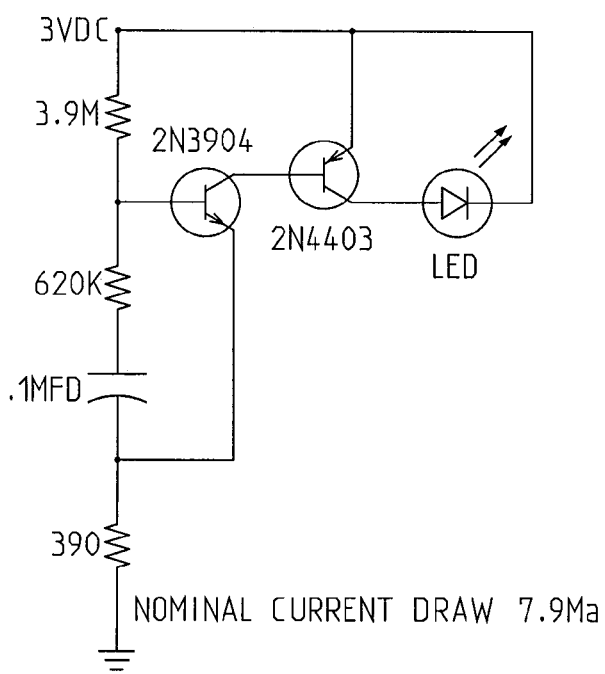
FIG. 7 is a schematic view of a first circuit that may be utilized in the monitors described herein.

Electrical circuit 118 is preferably an integrated circuit including an indicator such as a light emitting diode ("LED") 152 and or an audio device (not pictured), and a battery receiver 151 including a spring 153 located on an upper side 155 of a wafer base or circuit board 154, and an exposed circuit contact 158 located on a lower side 157 of circuit board 154. Circuit board 154 is preferably round to fit inside outlet housing 112. Circuit board 154 also has a plurality of apertures 156 defined therein sized and shaped to allow fluid to flow therethrough. (See FIG. 4e) Apertures 156 are aligned with pathways 160 in outlet housing 112 to further facilitate fluid flow. Batteries 120 are received within battery receiver 151 to provide power to circuit 118. A circuit gap is provided between contact 158 and conductive pad 146 to provide a discontinuity in circuit 118 that does not allow current to flow thereacross. The circuit gap is sized such that conductive pad 146 bridges the gap and closes the circuit when flexible portion 144 is deflected as discussed below. Circuit 118 is preferably a flasher circuit with short duty cycles to minimize current consumption and prolong battery life. An exemplary circuit is shown in FIG. 7.

Figure 8:
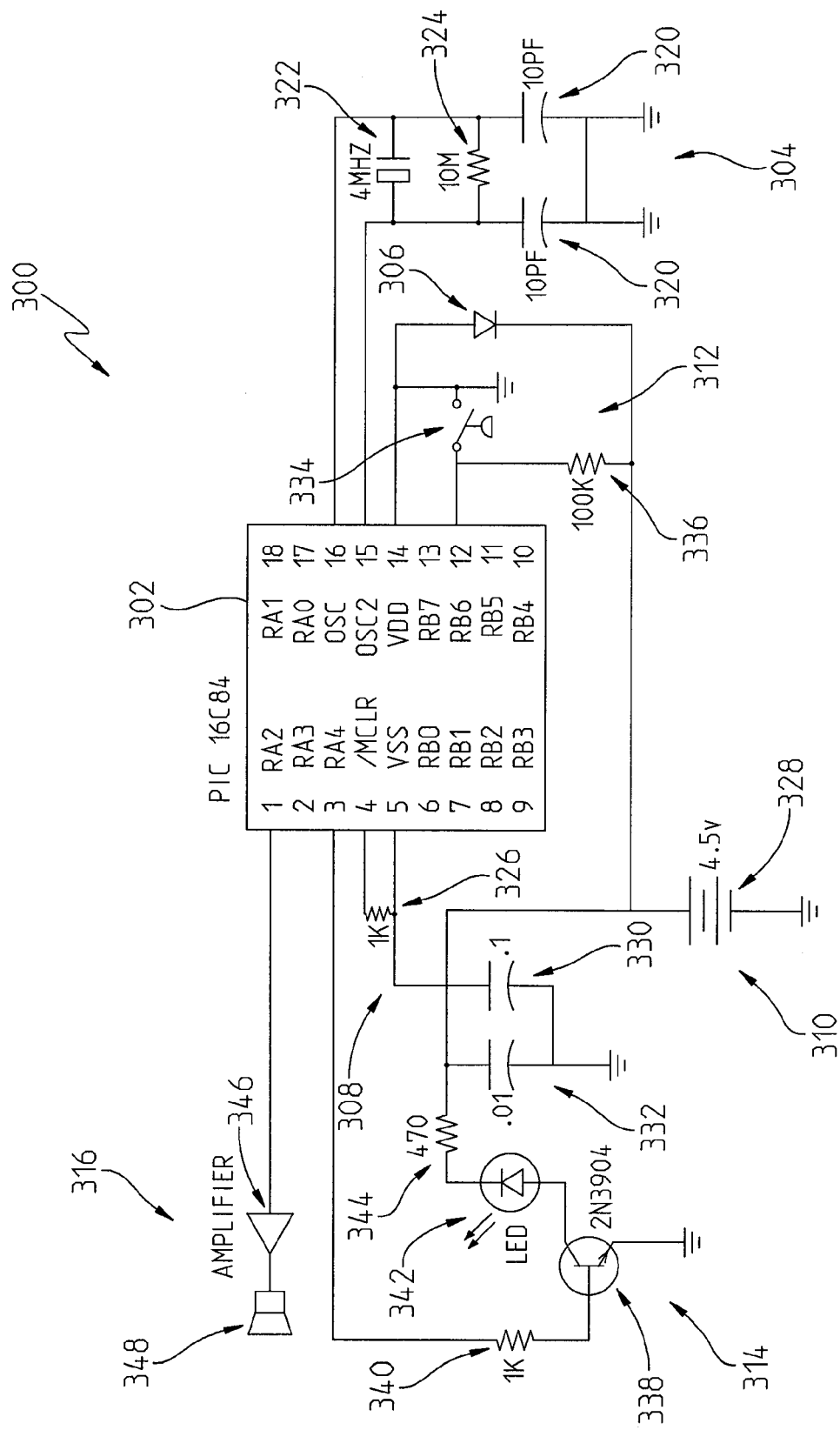
FIG. 8 is a schematic view of a second circuit that may be used with the monitors described herein.

Referring to FIG. 8, another exemplary circuit 300 is shown. Circuit 300 includes a controller 302, an oscillator circuit 304, a polarity protection diode 306 (to prevent accidental polarity reversals, a reset circuit 308, a power circuit 310, input circuit 312, a first output circuit 314, and a second output circuit 316. Controller 302 in the illustrated embodiment is a MicroChip PIC 16C84 MPU with a 4 MHz crystal frequency available from MicroChip located at 2355 West Chandler Blvd., Chandler, Ariz. 85224. In alternative embodiments, other controllers may be used.

Oscillator circuit 304 includes two 10 Pf capacitors 320, a 4 Mhz crystal 322 with a 10 Mohm resistor 324 in parallel. Reset circuit 308 includes a 1K resistor 326 pulling the MCLR pin of controller 302 high upon power up. Power circuit 310 includes three 1.5V batteries 328 connected in series, with two, 0.1 Mfd and 0.01 MFD, bypass capacitors 330, 332 in parallel. Input circuit 312 includes a pressure sensing switch 334 connected to RB6 pin of controller 302 with a 100 Kohm pull up resistor 336.

As discussed herein pressure sensing switch 334 may be implemented in a variety of configurations. Circuit 300 is configured for a pressure sensing switch 334 which is closed when the gas delivery system is operating properly and which is open when the gas delivery system is operating improperly. As will be appreciated in the discussion of exemplary software 400 (or firmware) (see FIGS. 9 and 10), controller 300 may be configured for a pressure sensing switch 334 which is open when the gas delivery system is operating properly and which is closed when the gas delivery system is operating improperly.

First output circuit 314 includes a NPN transistor 338 connected through a 1 Kohm base resistor 340, to port RA4 of controller 302. Transistor 338 turns on a LED 342 in series with a 470 ohm current limiting resistor 344. Second output circuit 316 includes an amplifier 346 connected to a piezoelectric sounding unit 348. Exemplary audio amplifier circuits include circuits that have a bandwidth of 0.5 to 3 Khz and can utilize a 5V DC coupled input.

As explained in more detail with reference to FIGS. 9 and 10, circuit 300 is configured to flash LED 342 when pressure sensing switch 334 is closed and if the pressure sensing switch has been open for a time greater than a threshold an alarm will sound with second output circuit 316. An exemplary threshold time is about 10 seconds to about 15 seconds.

Referring to FIG. 9, exemplary software 400 is shown for controller 302. It should be understood by those skilled in the art, that software 400 may be implemented as firmware in other embodiments. In step 402, controller 302 initializes circuit 300, such as by resetting counters discussed herein, setting port A as output, and setting port B as input.

In step 404, controller 302 reads the input to determine the state of pressure sensing switch 334. The step of reading the input includes reading the value of Port B Bit 6 followed by a second reading of Port B Bit 6 ("DeBounce"). If the input is high at block 406, indicating that the pressure in the respective fluid passage is low (the gas delivery system is operating improperly), controller 302 executes a time for alarm routine 408. If the input is low at block 406, indicating that the pressure in the respective fluid passage is not low (the gas delivery system is operating properly), controller 302 executes a flash LED routine 410.

Flash LED routine 410 includes the steps of turning on the respective LED (or other indicator), as represented by block 412, leaving the LED on for a given time period, as represented by block 414, and turning LED off, as represented by block 416. It should be appreciated that as long as the input at block 406 is low the flash LED routine 410 will be repeated, thus simulating a flashing LED. Also, in one example the separation between flashes and the duration of each flash are chosen to maximize battery life.

As stated above, circuit 300 is configured to wait for a predetermined time before sounding an alarm condition. This delay is implemented with time for alarm routine 408. Once a high condition is read on the input at block 406, time for alarm routine 408 is executed. As represented by step 418, a counter is incremented. Next, the input is read again, as represented by block 420. If the value of the counter exceeds a threshold number (the threshold being set based on the delay desired), then an alarm routine 422 is executed, as represented by block 424. If the threshold has not been exceeded, the routine increments the counter again if the value of the input is still high or resets the counter and returns to the main routine if the value of the input is low, as represented by block 426.

Figure 10:
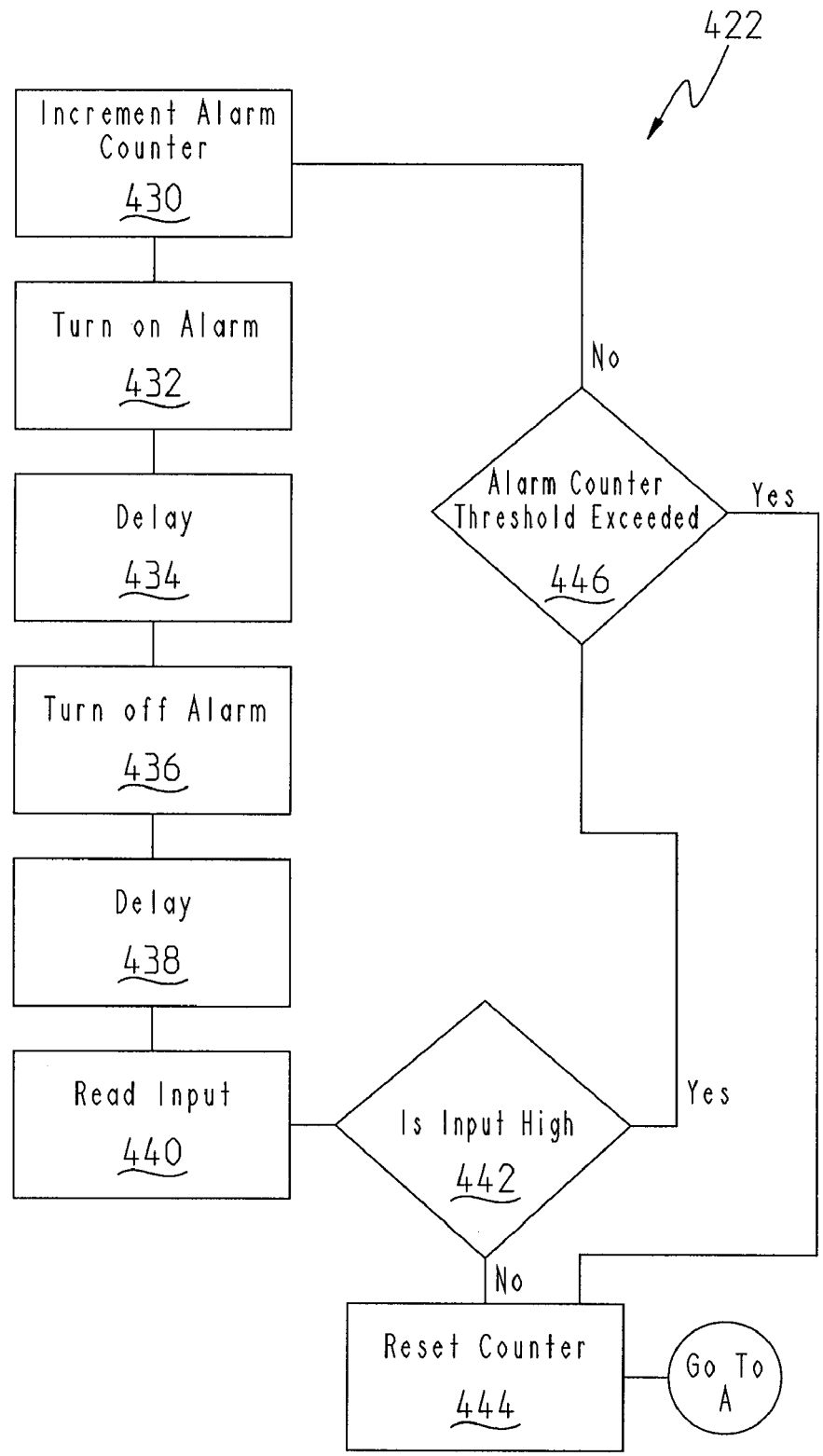

Referring to FIG. 10, an exemplary alarm routine 422 is shown. As represented by step 430, an alarm counter is incremented. An alarm, such as piezoelectric sounding unit 348, is turned on, as represented by block 432, for a predetermined time (such as about ¾ of a second), as represented by block 434. Next the alarm is turned off, as represented by block 436, for a predetermined time 9 such as about two seconds), as represented by block 438. The input is read again, as represented by block 440, to determine if the input has changed, as represented by block 442. If the input has changed to low, the alarm counter is reset, as represented by block 444, and the software returns to the main routine if the input remains high, it is determined if an alarm counter threshold has been exceeded, as represented by block 446. If the threshold has been exceeded the software returns to the main routine after resetting the counter until the alarm routine is initiated again. If the threshold has not been exceeded the counter is incremented as represented by block 430. The threshold value allows the system to control the duration of a given alarm sequence. In an alternative embodiment, the alarm threshold is removed and the alarm continues to sound indefinitely.

Returning to FIG. 2, housing seal 124 is illustratively a rubber annular element configured to be compressed between inlet housing 114 and outlet housing 112 when the housings 112,114 are threadably engaged. Housing seal 124 prevents fluid in the interior of the housing from escaping to outside the housing at the point where inlet housing 114 meets outlet housing 112. Housing seal 124 likewise prevents fluid on the exterior from entering the interior at the point where inlet housing 114 meets outlet housing 112.

Figure 3:
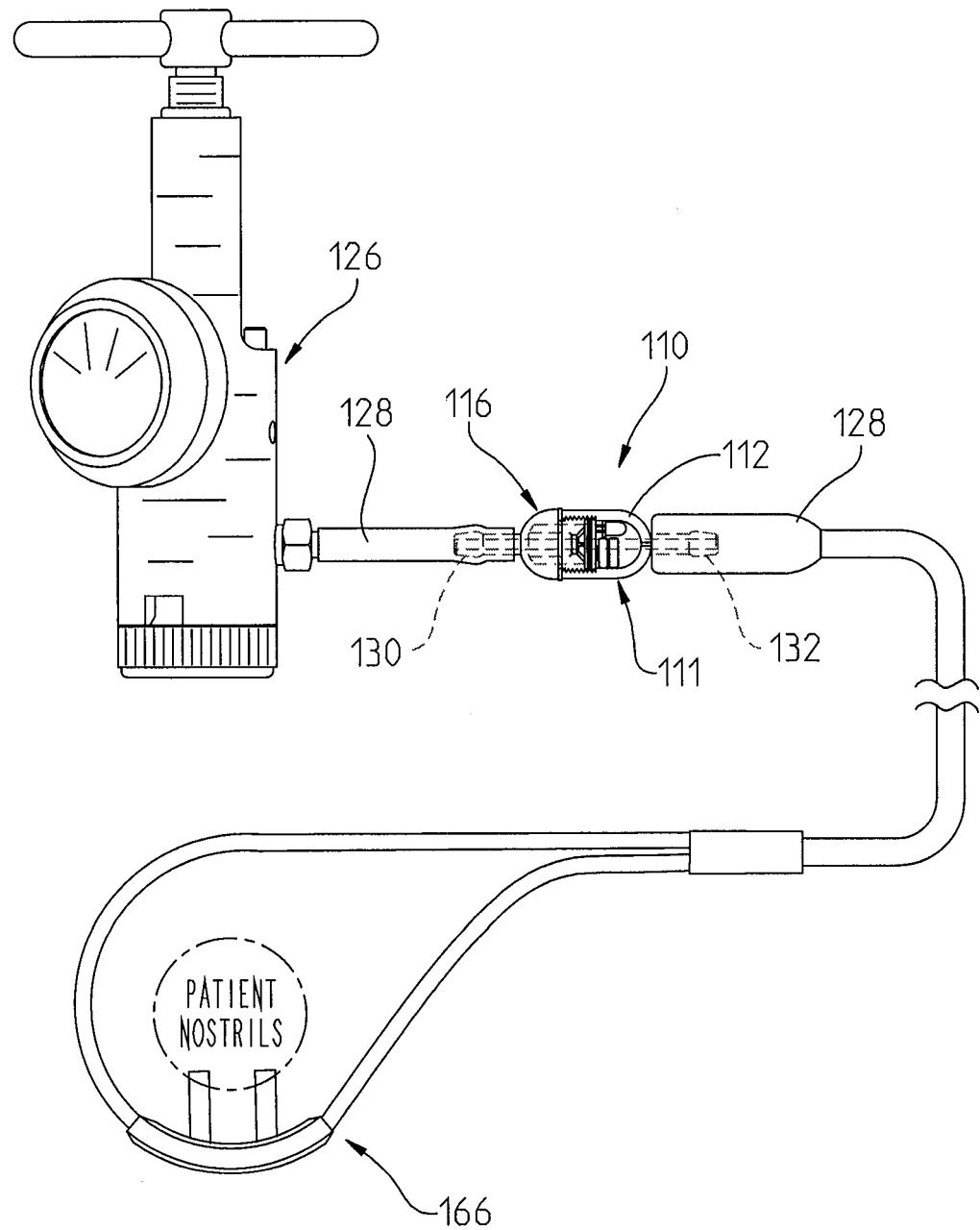
FIG. 3 is a sectional view of the fluid flow monitor with the cannula mount of FIG. 1 installed into a cannula coupled to a regulator.

Outlet housing 112 includes pathways 160, an internal threaded portion 162, barbed end 132, and an outlet 164. Pathways 160 are configured to direct fluid from beneath circuit 118 to outlet 164. Threaded portion 162 is configured to engage threaded portion 134 of inlet housing 114, 116 to, along with housing seal 124, provide a fluid tight housing. Barbed end 132 receives a piece of plastic tubing/cannula 128 thereon as shown in FIGS. 3 and 4.

In use, inlet housing 116 is connected to a cannula 128 (FIG. 3) or inlet housing 114 is connected to a regulator 126 (FIG. 4) and outlet housing 112 is connected to a cannula 128 which is in turn connected to a fluid utilizing device or fluid dispensing device 166. Once fluid flow is introduced to the cannula 128 or regulator 126 connected to input 131, pressure is applied to diaphragm 122. Diaphragm 122 is then deflected or biased from the first position to the second position such that conductive pad 146 moves toward circuit board 154 to engage contact 158 and complete circuit 118. Completing circuit 118 causes LED 152 to receive power from batteries 120 and emit light. Furthermore, distortion of the diaphragm 122 allows fluid to flow from input 131, around diaphragm 122 and circuit 118, to outlet 164. If fluid flow stops, or drops below a predetermined pressure, diaphragm 122 moves back to first position causing pad 146 to move away from contact 158, thereby opening circuit 118. The position of diaphragm 122 is dictated by the pressure developed therebehind.

While the present invention has been described as using circuit gap between contact 158 and conductive pad 146, it should be appreciated that other switch mechanism such as a piston that activates a switch or any other switching mechanism known in the art may be used. It is also envisioned to use different colored LED's 152 to indicate different gases. The placement of LED 152 within housing 111 allows light from LED 152 to be seen by a user. LED 152 light can be seen if housing 111 is transparent or translucent or if the light from LED 152 travels down a transparent/translucent outlet cannula 128.

Figure 5:
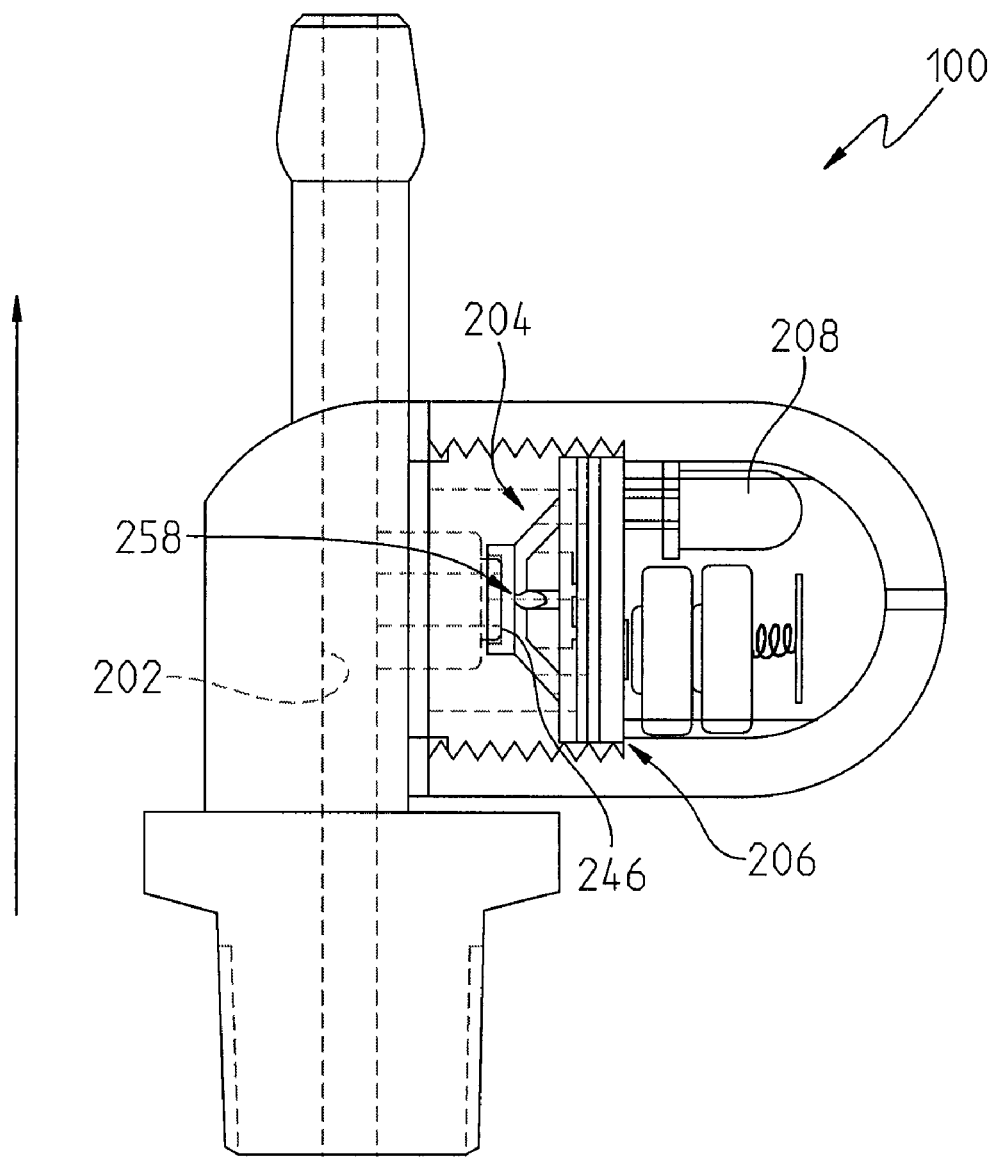
FIG. 5 is a side view of another exemplary fluid flow monitor or indicator.
Figure 6:
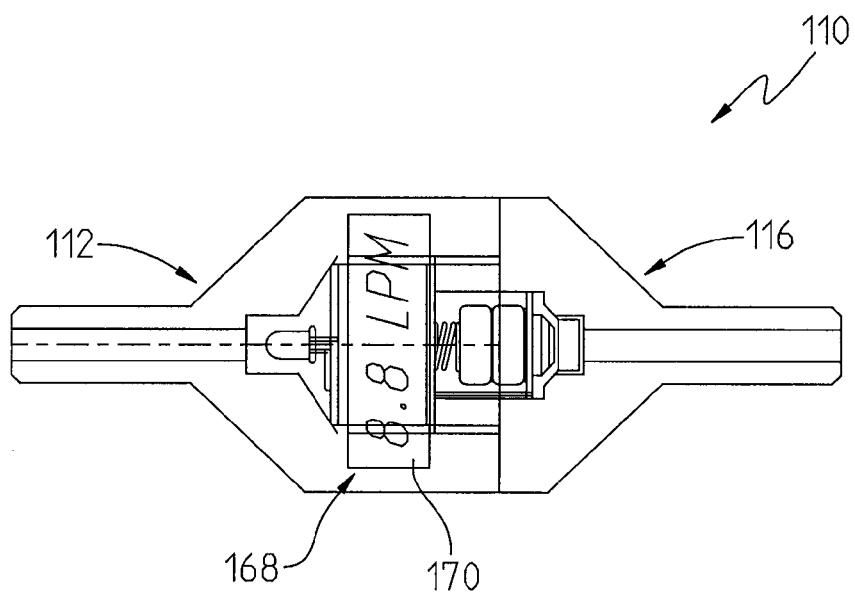
FIG. 6 is a side view of a further fluid flow monitor and flow meter.

In yet another embodiment, fluid flow indicator 110 includes a flow meter 168 as shown in FIG. 6. Flow meter 168 is preferably includes a digital readout 170 that displays the fluid flow speed. Flow meters which measure flow rate through a tube are generally known. Alternatively, the rate at which LED 152 flashes or a change in color of LED 152 may be used to indicate the fluid flow speed. Also, while the invention has been described as activating an indicator when fluid flow is present, embodiments are envisioned where indicators such as lights or buzzers are activated upon loss of fluid flow or fluid pressure. Such an embodiment is shown in FIG. 5.

The embodiment of FIG. 5 shows an indicator or monitor 200 such that an alarm sounds when indicator 200 becomes un-attached from the fluid source or a significant amount of fluid is escaping, or pressure in the fluid supply drops below a predetermined level. Pressure within a flow path 202 is translated to a diaphragm 204 similarly as it was for indicator 110. However, in FIG. 5, a conductive pad 246 is in a fixed position and normally engaged with a contact 258 on diaphragm 204 when diaphragm is in its first, unbiased position shown in FIG. 5. Pressure within flow path 202 distorts diaphragm 204 moves contact 258 away from pad 246 to de-activate circuit 206. However, distorted diaphragm 204 does not allow the passage of the gas thereby.

The gas is maintained beneath diaphragm 204. A loss of pressure in flow path 202 results in diaphragm 204 returning to its first, rest position and activating circuit 206 that in turn activates an indicator such as an LED 208 or a buzzer. Thus, a lack of connection to the fluid source, a leak in the system, or drop in pressure of the source will visually or sonically alert the user. The embodiment of FIG. 5 may be used concurrently with the embodiment of FIG. 1.

The back pressure indicator 200 of FIG. 5 is preferably mounted as close as possible to the regulator, because it relies on tubing restriction for proper operation. Typical tubing restrictions range from three to 15 inches of water. The electrical circuit is designed to give a battery life of about 28 days of continuous operation per set of batteries. This is accomplished with the use of short duty cycles and careful circuit design to minimize current consumption. In one embodiment, the back pressure indicator 200 emits a pattern of beeps for 3 minutes (or other preselected time) after the gas pressure is lost or until the gas pressure is restored. If the beeper timer has passed three minutes, the unit will not beep, until the gas has been restored. (Light operates.)

Other features of the invention include having LED 152, 208 flash at a first speed to indicate that the fluid flow is normal and flash at a second speed to indicate that fluid flow is abnormal. In another system, LED's 152, 208 flash at a certain speed and are detected by an alarm system that determines the speed or existence of flashing LED 152, 208 and alerts appropriate individuals upon noting an abnormal signal. Likewise, a preferably wireless transmitter may be placed in circuits 118, 206 to transmit signals to an alarm system in a facility. The transmission may alert appropriate individuals upon noting an abnormal flow signal.

Figures 11, 12:
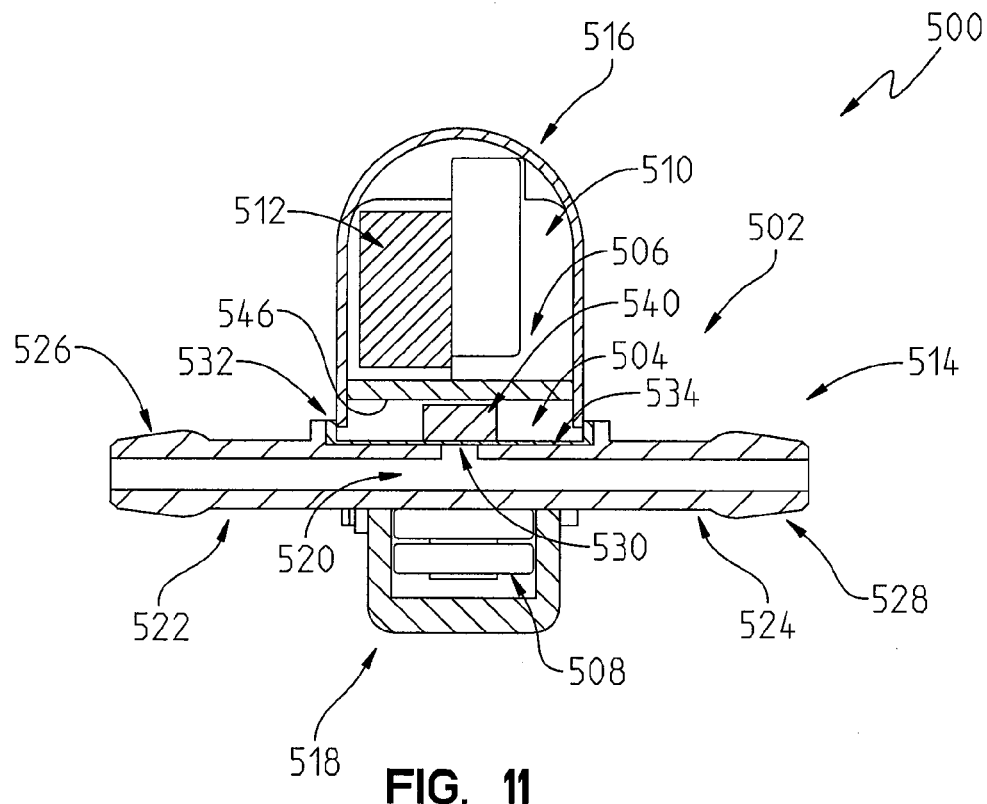
FIG. 11 is a side view of a yet further fluid flow monitor, the fluid flow monitor including a diaphragm shown in an unbiased position.
FIG. 12 is an end view of the fluid flow monitor of FIG. 11.
Figure 13:
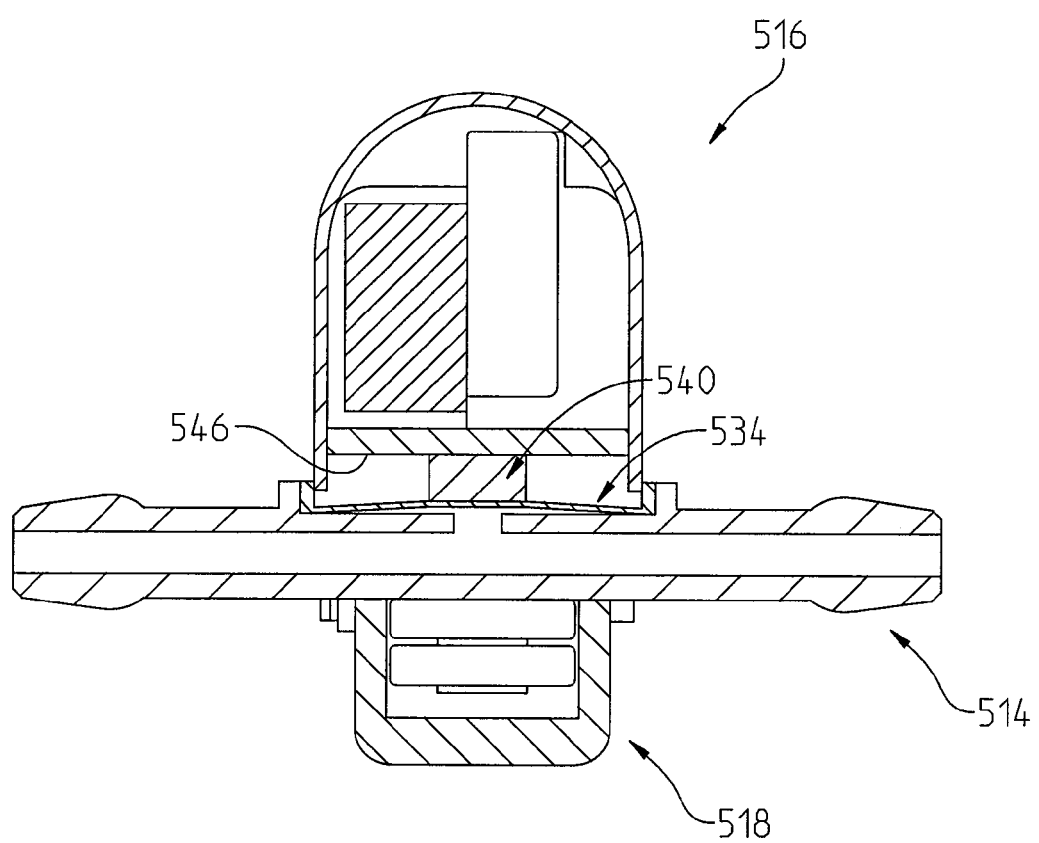
FIG. 13 is a side view of the fluid flow monitor of FIG. 11 illustrating the biased position of the diaphragm of FIG. 11.
Figure 14A:
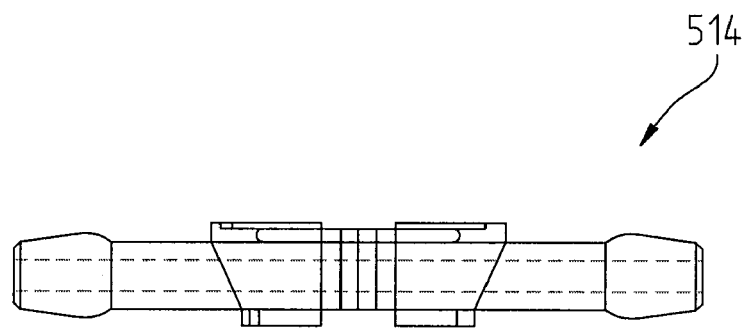
FIG. 14*a* is a side view of a body member of the fluid flow monitor of FIG. 11.
Figure 14B:
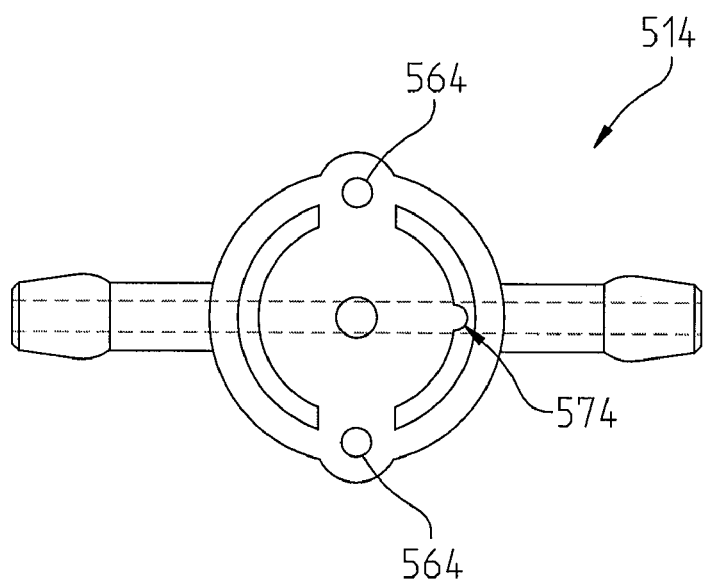
FIG. 14*b* is a bottom view of the body member of FIG. 14*a*.
Figure 14C:
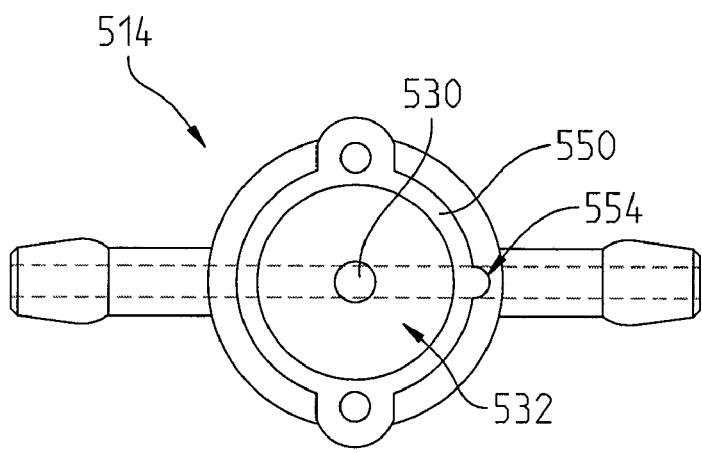
FIG. 14*c* is a top view of the body member of FIG. 14*a*.

Referring to FIGS. 11-13 another exemplary fluid flow monitor 500 is shown. Fluid flow monitor 500 includes a housing 502, a pressure sensitive switch 504, a controller 506, a power source 508, a first indicator 510, and a second indicator 512. In the illustrated embodiment, pressure sensitive switch 504, controller 506, power source 508, first indicator 510, and second indicator 512 are located with housing 502. In alternative embodiments, one or more of controller 506, power source 508, first indicator 510, and second indicator 512 may be located outside of housing 502.

Housing 502 illustratively includes a body member 514, a first removable housing member 516, and a second housing removable member 518. Referring to FIGS. 11 and 14a-c, body member 514 includes a fluid passage 520, an input coupler 522, and an output coupler 524. Input coupler 522 is shown with an end barb 526 for coupling body member 514 to a conduit. In an alternative embodiment, input coupler 522 is configured to be coupled to a directly to a flow regulator. Output coupler is shown with an end barb 528 for coupling body member 514 to a conduit. Fluid passage 520 connects input coupler 522 to output coupler 524 such that input coupler 522 and output coupler 524 are in fluid communication with each other.

Figure 15A:
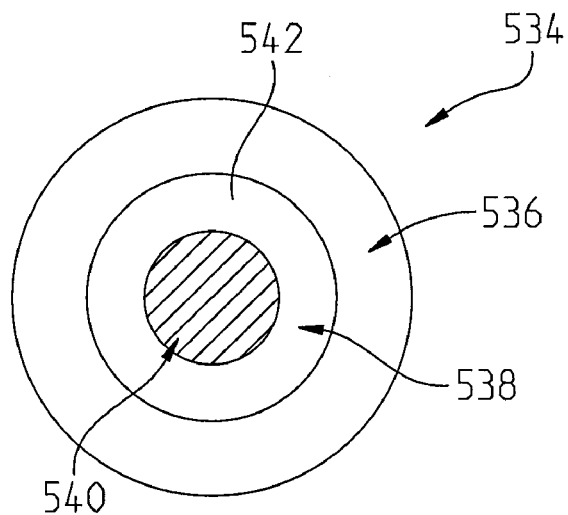
FIG. 15*a* is a top view of the diaphragm of the fluid flow monitor of FIG. 11.
Figure 15B:
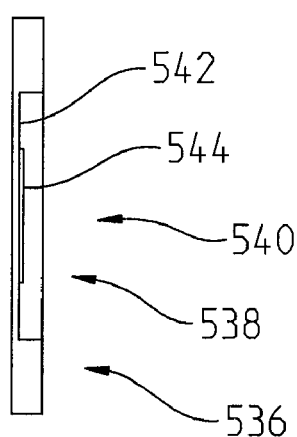
FIG. 15*b* is a side view of the diaphragm of FIG. 15*a*.

Body member 514 further includes a second fluid passage 530 which is in fluid communication with fluid passage 520. Body member 514 further includes a recess 532 sized to receive a diaphragm 534. Referring to FIG. 15a, a periphery 536 of diaphragm 534 is held in place by first housing member 516 which is removably coupled to body member 514. Diaphragm 534 makes a fluid tight seal with body member 514. A central portion 538 of diaphragm 534 is permitted to flex. As shown in FIG. 15b, in the illustrated embodiment central portion 538 has a reduced thickness compared to peripheral portion 536.

Central portion 538 supports, is coupled to, or has formed thereon a conductive pad 540 on its upper surface 542. In one embodiment, peripheral portion 536 and central portion 538 are made from a non-conductive material while at least a top surface 544 of conductive pad is made from a conductive material.

Diaphragm 534 is shown in FIG. 11 in a relaxed or first position corresponding fluid pressure in the fluid passage 520 and hence fluid passage 530 below the threshold amount (gas delivery system operating improperly). Diaphragm 534 is shown in FIG. 13 in a biased or second position corresponding to fluid pressure in fluid passage 520 and hence fluid passage 530 of at least the threshold amount (gas delivery system operating properly). The characteristics of diaphragm 534 are chosen such that conductive pad 540 contacts lower surface 546 at or above the threshold pressure for fluid passage 520.

In the biased position, conductive pad 540 is raised and contacts a both terminals of an open circuit or conductive grid 545 (see FIG. 16) located on lower surface 546 of a circuit board 548 which supports at least a portion of controller 506. By contacting both terminals of the circuit located on lower surface 546, conductive pad 540 completes the circuit. Controller 506 in a preferred embodiment includes the circuit 300 shown in FIG. 8 and the accompanying software discussed in connection with FIGS. 9 and 10.

Figure 16:
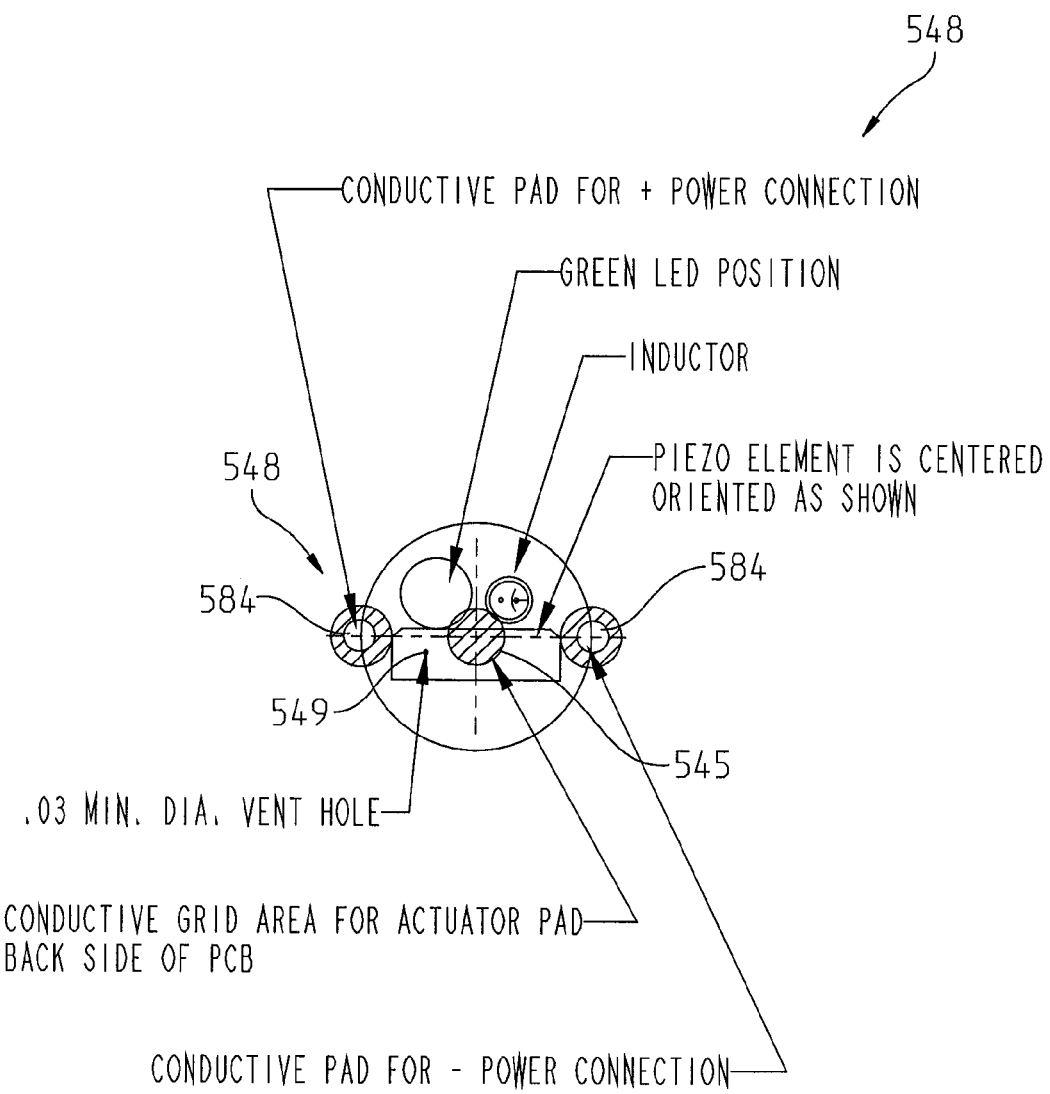
FIG. 16 is a top representative view of the circuit board of the fluid flow monitor of FIG. 11.
Figure 17B:
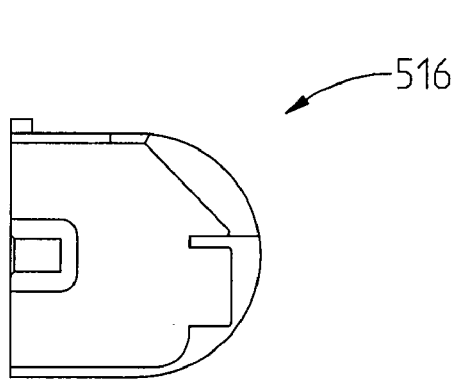
FIG. 17*b* is a first side view of the upper housing of FIG. 17*a*.
Figure 17A:
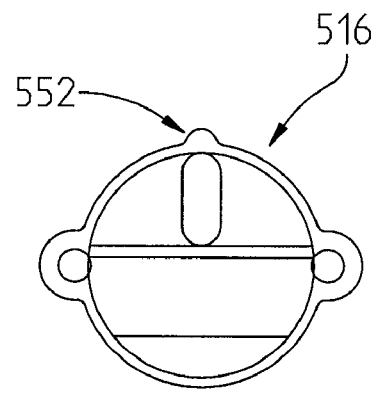
FIG. 17*a* is a top view of the upper housing of the fluid flow monitor of FIG. 11.
Figure 17C:
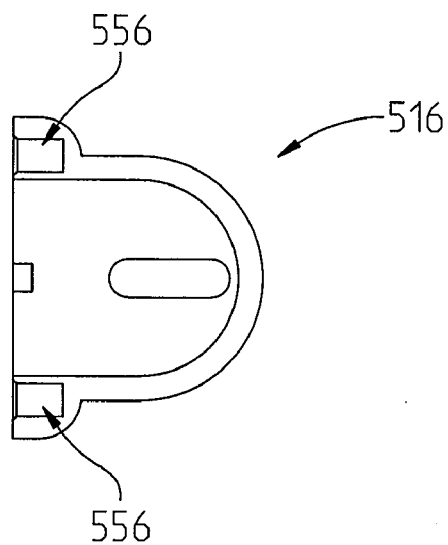
FIG. 17*c* is a second side view of the upper housing of FIG. 17*a*.
Figure 18A:
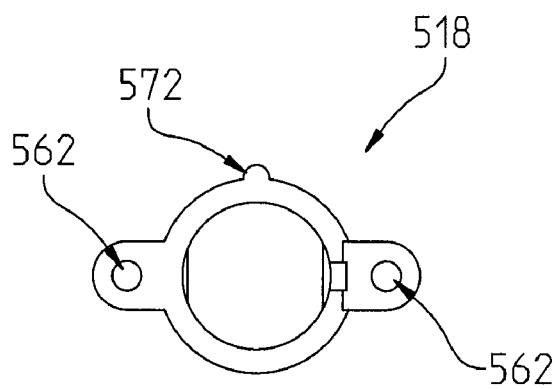
FIG. 18*a* is a top view of the lower housing of the fluid flow monitor of FIG. 11.
Figure 18B:
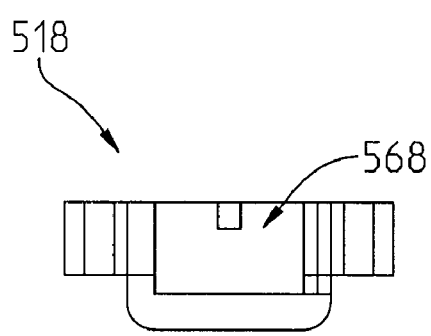
FIG. 18*b* is a first side view of the lower housing of FIG. 18*a*.
Figure 18C:
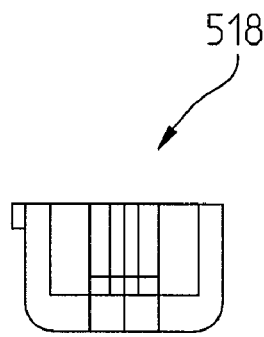
FIG. 18*c* is a second side view of the lower housing of FIG. 18*a*.

As shown in FIG. 16, circuit board 548 includes a vent hole 549 to permit air to pass from the lower side 546 of circuit board 548 to the other side of circuit board 548. Upper housing 516 further includes an opening (not shown) to permit sound from second indicator 512 to be more easily heard from an exterior of upper housing 516 and to place the interior the upper housing 516 in fluid communication with the exterior of the upper housing 516.

Referring to FIGS. 17a-c and 14c, upper housing 516 is configured to be received in a groove 550 of body member 514. Further upper housing 516 and body member 514 each includes a key feature 552, 554 to orient upper housing 516 relative to body member 514. Upper housing 516 additionally includes a partially contoured interior surface configured to locate portions of circuit board 548, first indicator 510, and second indicator 512. Further, at least a portion of upper housing is partially translucent or transparent to permit first indicator 510 to be visible from an exterior of upper housing 516.

Upper housing 516 further includes two threaded portions 556 each sized to threadably receive a respective coupler 560. Couplers 560 are received by openings 562 in lower housing 518 and corresponding openings 564 in body member 514. By threading couplers 560 into upper housing 516, both of lower housing 518 and upper housing 516 are coupled to body member 514.

Referring to FIGS. 18a-c and FIG. 11, lower housing 518 further includes a battery receiving cavity 568 sized to receive batteries 508. Lower housing 518 is configured to be received in a groove 570 of body member 514. Further lower housing 518 and body member 514 each includes a key feature 572, 574 to orient lower housing 518 relative to body member 514.

Referring to FIG. 12, lower housing 518 further includes a first battery contact 576 having a first end 577 positioned proximate to a negative terminal of batteries 508 and a second end 578 positioned proximate to one of couplers 560 and a second battery contact 580 having a first end 581 positioned proximate to a positive terminal of batteries 508 and a second end 582 positioned proximate to the other of couplers 560.

Coupler 560 are made of a conductive material. In addition to coupling upper housing 516 and lower housing 518 to body member 514, couplers 560 are received in openings 584 (see FIG. 16) of circuit board 548, the openings 584 also having conducting portions. As such couplers 560 provide power from power source 508 to controller 506, first indicator 510, and second indicator 512 through the connection of each coupler with the respective opening in circuit board 548 and the connection with the respective battery contact 576, 580.

It will be appreciated that by having couplers 560 couple power source 508 to controller 506, first indicator 510, and second indicator 512, power source 508 may be positioned on an opposite side of fluid passage 520 than controller 506, first indicator 510, and second indicator 512 while still maintaining isolation of the electrical components from fluid passage 520.

Figure 19A:
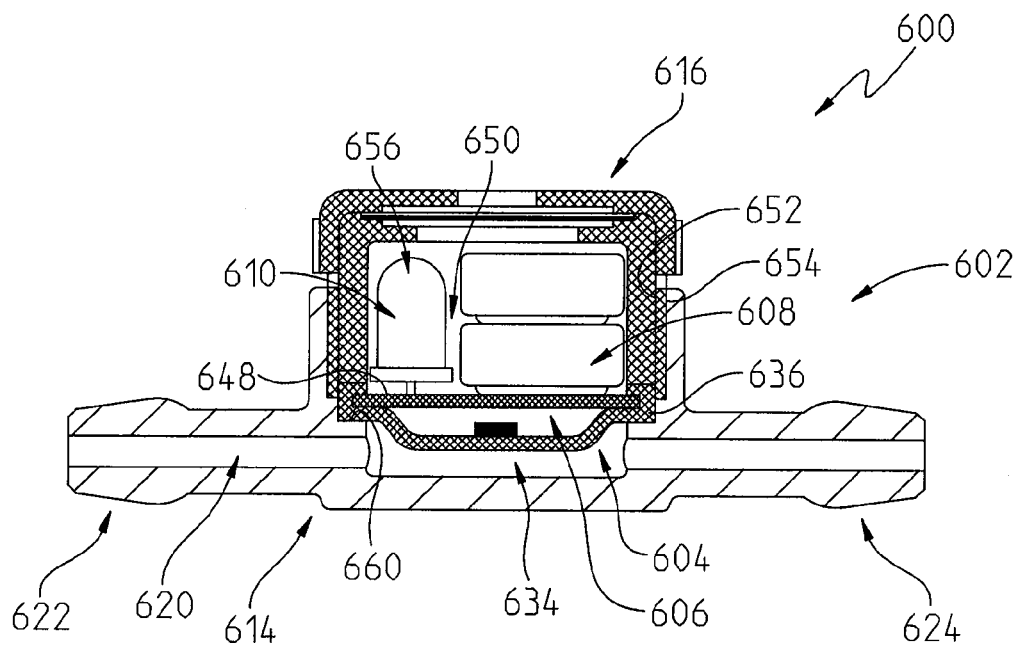
FIG. 19*a* is a side view of a still further exemplary embodiment of a fluid flow monitor.
Figure 19B:
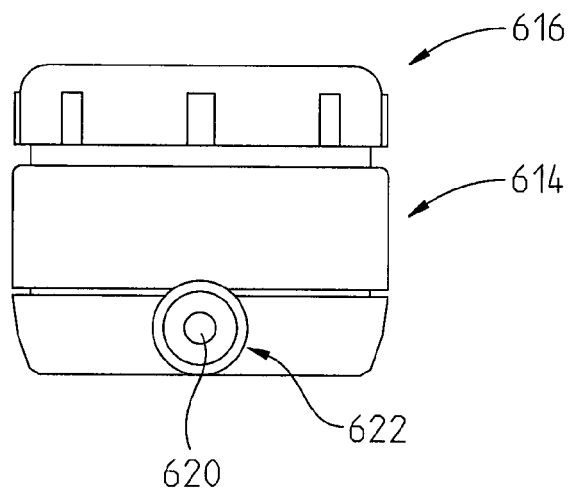
FIG. 19*b* is a side view of the fluid flow monitor of FIG. 19*a*.

Referring to FIGS. 19a and 19b, another exemplary fluid flow monitor 600 is shown. Fluid flow monitor 600 includes a housing 602, a pressure sensitive switch 604, a controller 606, a power source 608, a first indicator 610, and a second indicator (not shown). Housing 602 includes a body member 614 having a fluid passage 620, an input coupler 622 and an output coupler 624 and an upper housing 616. Fluid flow monitor 600 is generally similar to fluid flow monitor 500 except that all of the components pressure sensitive switch 604, controller 606, power source 608, first indicator 610, and second indicator (not shown) are located on one side of fluid passage 620.

Pressure sensing switch 604 of fluid flow monitor includes a diaphragm 634. Diaphragm 634 is generally similar to diaphragm 534 except that diaphragm 634 is a generally constant thickness and the peripheral portion 636 of diaphragm 634 is configured to be clipped around circuit board 648. The interaction and operation of pressure sensing switch 604, controller 606, first indicator 610, and second indicator (not shown) is generally similar to the interaction and operation of pressure sensing switch 504, controller 506, first indicator 510, and second indicator 512 of fluid flow monitor 500.

Body member 614 includes a recess 650 sized to receive pressure sensitive switch 604, controller 606, power source 608, first indicator 610, and second indicator (not shown). Recess 650 further includes an internally threaded side wall 652 configured to threadably receive matching threaded portion 654 on upper housing 616. Upper housing 616 includes a recess 656 to receive power source 608, first indicator 610, and second indicator (not shown). By threadably advancing upper housing 616 into recess 650 of body member 614, upper housing 616 contacts diaphragm 634 and causes diaphragm to form a fluid tight seal with a lip 660 of body member 614.

Figure 20:
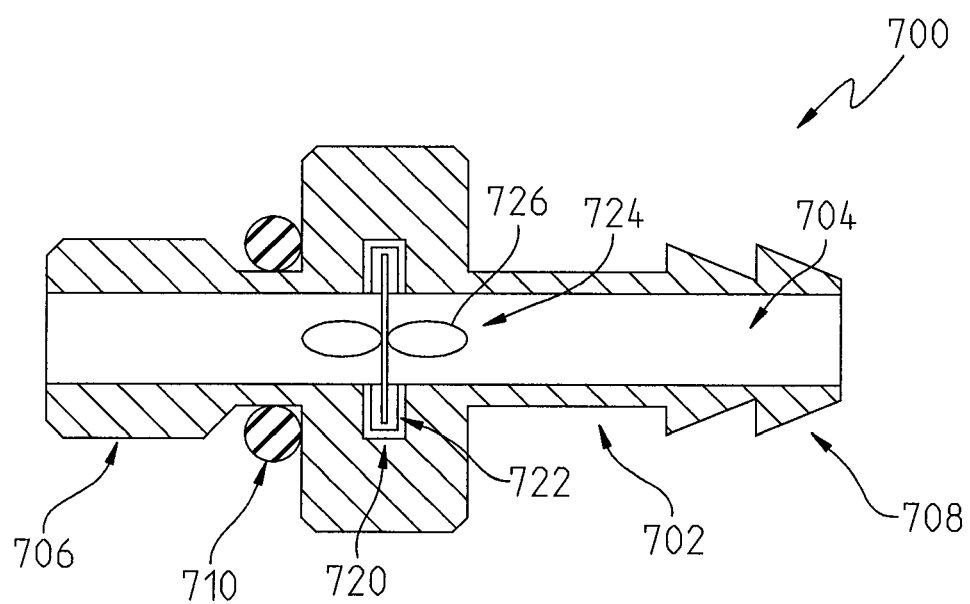
FIG. 20 is a side view of a mechanical fluid flow monitor.

Referring to FIG. 20 a mechanical flow indicator 700 is shown. Flow indicator 700 includes a housing 702 (preferable made of two components (not shown) coupled together) having a central fluid passage 704, an input coupler 706, and an outlet coupler 708. Input coupler 706 is shown configured to couple directly to a flow regulator. However, input coupler 706 may be configured with a hose barb like the hose barb shown as part of output coupler 708 or like hose barb 526 of input coupler 522. As shown input coupler 706 is to be threadably received within an opening (not shown) of a flow regulator until seal 710 creates a seal between flow indicator 700 and flow regulator (not shown).

Housing 702 further includes a recess 720 sized to receive a bearing 722. Supported by bearing 722 is a fan 724 having a plurality of fan blades 726. One of fan 724 and bearing 722 or one of bearing 722 and housing 702 is freely rotatable relative to the other of fan 724 and bearing 722 or the other of bearing 722 and housing 702. When fluid is passed along fluid passage 720 from input coupler 724 toward output coupler 726, the fluid impinges upon fan blades 726 of fan 724 causing fan 722 to rotate relative to housing 702. Housing 702 is preferably at least partially translucent or transparent such that the rotation of fan 724 relative to housing 702 is visible to an outside observer and provides a visual cue that fluid is flowing through fluid passage 704. In one example, fan 724 is made from one piece of wireform.

Figure 21:
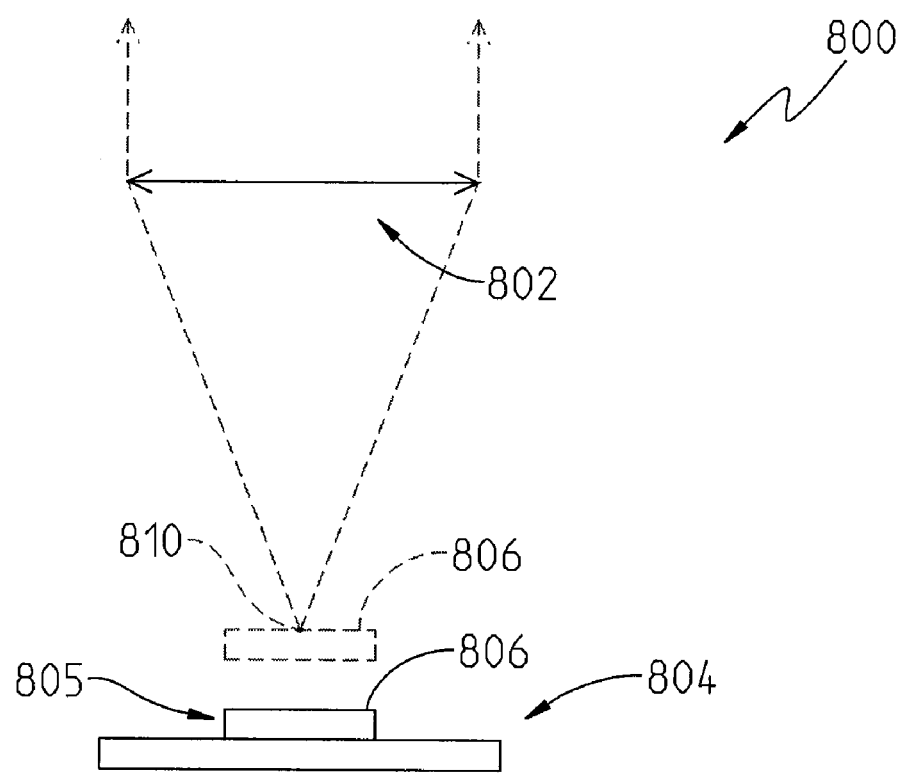
FIG. 21 is a representation of a further mechanical fluid flow indicator or monitor, wherein the movement of a colored disk indicates the flow of fluid through the fluid passage.

Referring to FIG. 21, a representation of another exemplary fluid flow indicator 800 is shown. Fluid flow indicator 800 is generally similar to fluid flow indicator 500 except that controller 506, power source 608, first indicator 610, and second indicator (not shown) are replaced with a collimating lens 802. Diaphragm 804 is generally similar to diaphragm 534 in that its movement is responsive to the pressure in the fluid passage (not shown) of fluid flow indicator 800. Further conductive pad 540 is replaced with a pad 805 having a surface 806 which is at least partially colored.

In operation, when the pressure in the fluid passage (not shown) is below the threshold value (gas delivery system is not operating properly), diaphragm 804 is in a relaxed position and colored surface 806 is spaced apart from a focus 810 of collimating lens 802. When the pressure in the fluid passage (not shown) is at or above the threshold value (gas delivery system is operating properly), diaphragm 804 is in a biased position and colored surface 806 (shown in phantom) is generally located at focus 810 of collimating lens 802. When colored surface 806 is at focus 810, an observer from the opposite side of lens 802 (outside of the housing) will see a large, if not full view image of colored surface 806. When colored surface 806 is spaced apart from focus 810, an observer of the opposite side of lens 802 will see a small or no image of colored surface 806.

Figure 22:
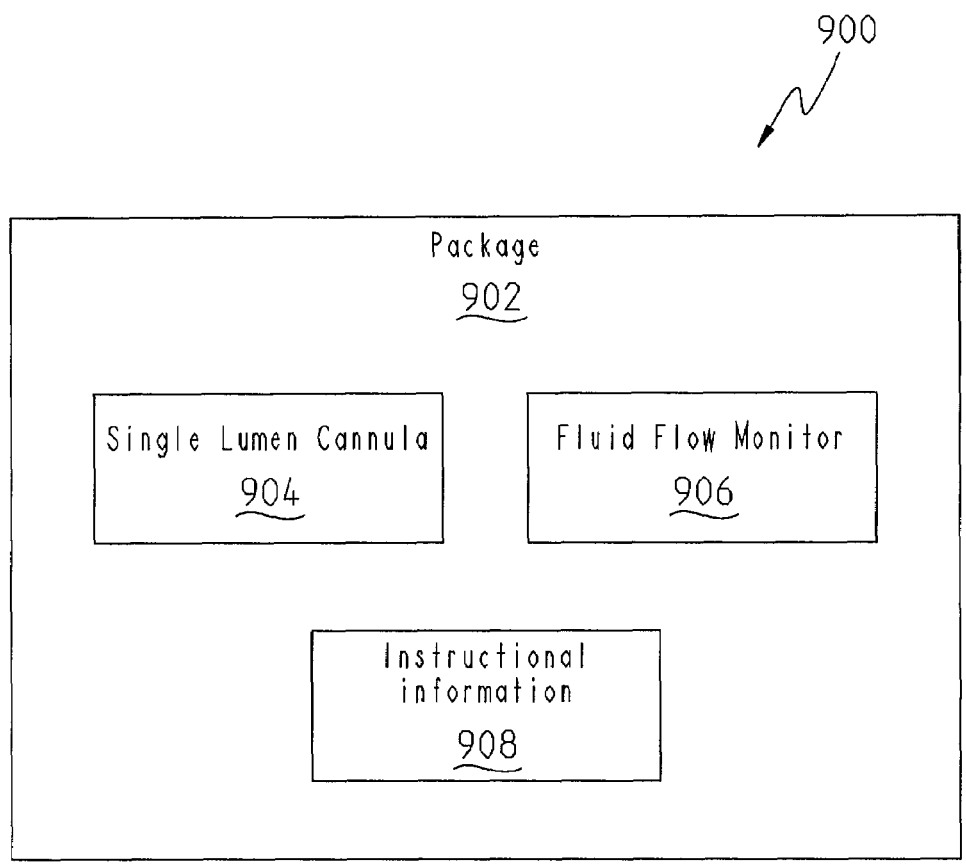
FIG. 22 is a kit containing a single lumen cannula, a fluid flow monitor, and instructional information contained within a package.

In a preferred embodiment shown in FIG. 22, a kit 900 is provided including a package 902 containing a single lumen cannula 904, a fluid flow monitor 906, and an instructional information 308. Single lumen cannula 904 and fluid flow monitor 906 are each sterilized for use with a patient. The sterilized single lumen cannula 904 and fluid flow monitor 906 are sealed in package 902 along with instructional information 908. Package 902 in one example is hated sealed along two edges to enclose the single lumen cannula 904, fluid flow monitor 906 and instruction information 908. In one example, instructional information 908 is provided on an information sheet or pamphlet either placed inside package 902 with single lumen cannula 902 and fluid flow monitor 904 or attached to an exterior of package 902. In another example, instructional information is printed onto a surface of package 902. It should be appreciated that kit 900 provides a caregiver with a disposable system for delivering oxygen to a patient with a disposable single lumen cannula 902 and monitoring the delivery of oxygen to the patient with a disposable fluid flow monitor 904. Fluid flow monitor 904, in one example, may be one of fluid flow monitors 10,110, 200, 500, 600, 700, and 800.

The present invention is specifically noted as having applicability in the fields of medical gases such as oxygen, air, nitrous oxide, nitrogen, carbon dioxide, or helium for use in patient care in the home or in a care facility. Further, applicability in the fields of welding, in transmittal of natural gas, and in burning gas is contemplated. However, the present invention is not limited to such areas and uses.

Although the present invention has been described in detail with reference to preferred embodiments, variations and modifications exist within the scope and spirit of the present invention as described and defined in the following claims.

The invention claimed is:

1. A gas flow monitor comprising:
a housing having a fluid passage, an inlet and an outlet, the fluid passage configured to pass a gas introduced at the inlet to the outlet;
a controller contained within the housing;
a first indicator contained within the housing;
a pressure sensitive switch in fluid communication with the fluid passage, the pressure sensitive switch having a first position indicating that the fluid passage contains at least a threshold pressure of a gas introduced through the inlet and a second position indicating the absence of a threshold pressure of a gas in the fluid passage, wherein the controller is configured to provide a first indication with the first indicator in response to the pressure sensitive switch being in the first position, wherein the housing includes a body member including the fluid passage, a first removable housing member configured to be coupled to the body member, and a second removable housing member configured to be coupled to the body member, the first removable housing member configured to receive the controller and the first indicator, the second removable housing configured to receive a portable power supply, the portable power supply being electrically coupled to the controller and the first indicator.

2. The gas flow monitor of claim 1, wherein the first indicator is a visual indicator and the housing is configured to permit observation of the visual indicator from an exterior of the housing.

3. The gas flow monitor of claim 1, further comprising a second indicator and wherein the controller is configured to provide a second indication with the second indicator in response to the pressure sensitive switch being in the second position.

4. The gas flow monitor of claim 3, wherein the second indicator is an audio indicator and the second indication is at least a first sound emitting from the audio indicator.

5. The gas flow monitor of claim 1, further comprising a wireless transmitter and wherein the controller is configured to generate an alarm signal to be emitted by the wireless transmitter in response to the pressure sensitive switch being in the second position.

6. The gas flow monitor of claim 1, wherein the indicator is a wireless transmitter configured to transmit a first signal to a monitoring network capable of alerting appropriate individuals, the first signal corresponding to one of the pressure sensitive switch being in the first position and in the second position.

7. The gas flow monitor of clam 1, wherein the body member includes a first opening and a second opening, each of the first and second openings configured to receive a respective one of a first coupler and a second coupler, each of the first coupler and the second coupler being configured to couple the first removable housing and the second removable housing to the body member, the first and second couplers further being configured to electrically couple the portable power supply and the controller.

8. The gas flow monitor of claim 1, wherein the first indicator is a visual indicator.

9. The gas flow monitor of claim 8, wherein the visual indicator is a light emitting diode.

10. The gas flow monitor of claim 9, wherein the light emitting diode is positioned within the housing so as to pass light down a portion of a fluid conduit coupled to the housing.

11. The gas flow monitor of claim 1, wherein the pressure sensitive switch includes a diaphragm and an electrically conductive portion, the electrically conductive portion being positioned to a first side of the diaphragm and spaced apart from the fluid passage which is positioned to a second side of the diaphragm.

12. A gas flow monitor configured to be coupled in-line to a gas delivery system configured to convey a regulated amount of gas from a gas source to a patient, the gas delivery system including a first portion coupled to the gas source and a second portion coupled to a fluid dispensing device, the gas flow monitor comprising:
a housing having a fluid passage, an inlet and an outlet, the fluid passage configured to pass a gas introduced at the inlet to the outlet, the inlet configured to be coupled to the first portion of the gas delivery system and the outlet configured to be coupled to the second portion of the gas delivery system;
an indicator contained within the housing, the indicator configured to provide a first indication to indicate that the gas is being passed from the inlet to the outlet of the housing, the first indication being visible from an exterior of the housing; and
a lens coupled to the housing and a pressure sensitive element in fluid communication with the fluid passage, the pressure sensitive element including a colored portion positioned in a first position indicating that the fluid passage contains at least a threshold pressure of the gas introduced through the inlet and a second position indicating the absence of a threshold pressure of the gas in the fluid passage, the first position corresponds to the colored portion being positioned generally at a focus of the lens and the second position corresponds to the colored portion being spaced apart from the focus of the lens.

13. A gas flow monitor comprising:
a housing having a fluid passage, an inlet and an outlet, the fluid passage configured to pass a gas introduced at the inlet to the outlet, the housing including a body member including the fluid passage and a first engagement member and a removable housing member removably coupled to the body member, the removable housing member including a second engagement member, the first engagement member and the second engagement member cooperating to couple the removable housing member to the body member;
a controller contained within the housing;
a portable power supply contained within the housing;
a first indicator;
a pressure sensitive switch in fluid communication with the fluid passage, the pressure sensitive switch having a first position indicating that the fluid passage contains at least a threshold pressure of a gas introduced through the inlet and a second position indicating the absence of a threshold pressure of a gas in the fluid passage, wherein the controller is configured to provide a first indication with the first indicator in response to the pressure sensitive switch being in the first position, wherein the body member and the removable housing member are configured to capture the controller, the portable power supply, and the indicator within an exterior of the housing when the removable housing member is coupled to the body member through the first engagement member and the second engagement member.

14. The gas flow monitor of claim 13, wherein the pressure sensitive switch includes a diaphragm in fluid communication with the fluid passage, the diaphragm including a conductive portion which is configured to electrically complete a circuit being monitored by the controller when the pressure sensitive switch is in the first position.

15. The gas flow monitor of claim 13, wherein the pressure sensitive switch includes a diaphragm in fluid communication with the fluid passage, the diaphragm including a conductive portion which is configured to electrically complete a circuit being monitored by the controller when the pressure sensitive switch is in the second position.

16. The gas flow monitor of claim 13, wherein the fluid passage is isolated from the controller such that the gas in the passage is insulated from a plurality of electrical components of the controller.

17. The gas flow monitor of claim 13, further comprising a flow meter that displays at least one of a flow volume in the fluid passage and a flow velocity in the fluid passage, the flow meter being coupled to the controller which determines at least one of the flow volume in the fluid passage and the flow velocity in the fluid passage.

18. The gas flow monitor of claim 13, wherein the first engagement member and the second engagement member are threadably coupled.

19. The gas flow monitor of claim 13, wherein the pressure sensitive switch includes a diaphragm and an electrically conductive portion, the electrically conductive portion being positioned to a first side of the diaphragm and spaced apart from the fluid passage which is positioned to a second side of the diaphragm.

20. The gas flow monitor of claim 13, wherein the first indicator is a visual indicator and the housing is configured to permit observation of the visual indicator from an exterior of the housing.

21. The gas flow monitor of claim 13, further comprising a second indicator and wherein the controller is configured to provide a second indication with the second indicator in response to the pressure sensitive switch being in the second position.

22. The gas flow monitor of claim 13, wherein the second indicator is an audio indicator and the second indication is at least a first sound emitting from the audio indicator.

23. The gas flow monitor of claim 13, further comprising a wireless transmitter and wherein the controller is configured to generate an alarm signal to be emitted by the wireless transmitter in response to the pressure sensitive switch being in the second position.

24. The gas flow monitor of claim 13, wherein the first indicator is a wireless transmitter configured to transmit a first signal to a monitoring network capable of alerting appropriate individuals, the first signal corresponding to one of the pressure sensitive switch being in the first position and in the second position.

* * * * *